(12) United States Patent
Silverman et al.

(10) Patent No.: US 9,212,144 B2
(45) Date of Patent: Dec. 15, 2015

(54) 2-AMINOQUINOLINE-BASED COMPOUNDS FOR POTENT AND SELECTIVE NEURONAL NITRIC OXIDE SYNTHASE INHIBITION

(71) Applicant: Northwestern University, Evanston, IL (US)

(72) Inventors: Richard B. Silverman, Winnetka, IL (US); Maris A. Cinelli, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/594,925

(22) Filed: Jan. 12, 2015

(65) Prior Publication Data
US 2015/0210644 A1 Jul. 30, 2015

Related U.S. Application Data

(60) Provisional application No. 61/964,645, filed on Jan. 10, 2014.

(51) Int. Cl.
*C07D 215/38* (2006.01)
*A61K 31/47* (2006.01)

(52) U.S. Cl.
CPC .................... *C07D 215/38* (2013.01)

(58) Field of Classification Search
CPC .............................. C07D 215/38; A61K 31/47
See application file for complete search history.

(56) References Cited

U.S. PATENT DOCUMENTS

| | | | | |
|---|---|---|---|---|
| 6,787,558 B2 * | 9/2004 | Klug et al. | ..................... | 514/313 |
| 7,012,073 B2 * | 3/2006 | Klug et al. | ............... | 514/217.07 |
| 7,064,134 B2 * | 6/2006 | Klug et al. | ..................... | 514/312 |
| 7,166,589 B2 * | 1/2007 | Klug et al. | ..................... | 514/218 |

OTHER PUBLICATIONS

Rosen, G. M.; Tsai, P.; and Pou, S., "Mechanism of free-radical generation by nitric oxide synthase", Chem. Rev. 2002, 102 (4), 1191-1199.

Ji, H.; Tan, S.; Igarashi, J.; Li, H.; Derrick, M.; Martásek, P.; Roman, L. J.; Vasquez-Vivar, J.; Poulos, T. L.; and Silverman, R. B., "Selective Neuronal Nitric Oxide Synthase Inhibitors and the Prevention of Cerebral Palsy", Ann. Neurol. 2009. 65, 209-217.

Labby, K. J.; Xue, F.; Kraus, J. M.; Ji, H.; Mataka, J.; Li, H.; Martásek, P.; Roman, L. J.; Poulos, T. L.; and Silverman, R.B., "Intramolecular hydrogen bonding: A potential strategy for more bioavailable inhibitors of neuronal nitric oxide synthase", Bioorg. Med. Chem. 2012, 20, 2435 2443.

Hevel, J. M. and Marletta, M.A., "Nitric Oxide Synthase assays in Methods in Enzymology", 1994, 233, 250 258.

* cited by examiner

*Primary Examiner* — D M Seaman
(74) *Attorney, Agent, or Firm* — Reinhart Boerner Van Deuren s.c.

(57) ABSTRACT

Various 2-aminoquinoline compounds as can be used, in vivo or in vitro, for selective inhibition of neuronal nitric oxide synthase.

35 Claims, 8 Drawing Sheets

2-AMINOQUINOLINE-BASED COMPOUNDS FOR POTENT AND SELECTIVE NEURONAL NITRIC OXIDE SYNTHASE INHIBITION

This application claims priority to and the benefit of Application Ser. No. 61/964,645, filed Jan. 10, 2014—the entirety of which is incorporated herein by reference.

This invention was made with government support under grant number R01 GM049725 awarded by the National Institutes of Health. The government has certain rights in the invention.

BACKGROUND OF THE INVENTION

The term neurodegenerative disorder is used to describe diseases characterized by the progressive breakdown of neuronal function and structure. This term encompasses disorders such as Alzheimer's, Parkinson's, and Huntington's diseases, as well as amyotrophic lateral sclerosis (ALS), among others, although neuronal damage is also associated with stroke and ischemic events, cerebral palsy, and head trauma. Although the human and economic cost of neurodegeneration continues to be astronomical, treatment is largely limited to palliative care and prevention of symptom progression. Therefore, there is a constant demand for novel and effective approaches to slow or prevent the progression of these diseases.

One target under investigation is neuronal nitric oxide synthase (nNOS). Nitric oxide (NO) is an important second messenger in the human body, and dysregulation of its production is implicated in many pathologies. NO is produced by the nitric oxide synthase enzymes, of which there are three isoforms: endothelial nitric oxide synthase (eNOS), which regulates blood pressure and flow, inducible nitric oxide synthase (iNOS), involved in immune system activation, and nNOS, which is required for normal neuronal signaling. Nonetheless, over-expression of nNOS in neural tissue and increased levels of NO can result in protein nitration and oxidative damage to neurons, especially if peroxynitrite is formed from excess NO. Indeed, overexpression of nNOS or excess NO has been implicated in or associated with many neurodegenerative disorders. The inhibition of nNOS is, therefore, a viable therapeutic strategy for preventing or treating neuronal damage.

All NOS enzymes are active only as homodimers. Each monomer consists of both a reductase domain with FAD, FMN, and NADPH binding sites, and a heme-containing oxygenase domain, where the substrate (L-arginine) and cofactor (6R)-5,6,7,8-tetrahydrobiopterin ($H_4B$) bind. Activated and regulated by calmodulin binding, electron flow proceeds from one monomer's reductase domain to the other's oxygenase domain, catalyzing the oxidation of arginine to citrulline with concomitant production of NO. (See, Rosen, G. M.; Tsai, P.; and Pou, S. Mechanism of free-radical generation by nitric oxide synthase. *Chem. Rev.* 2002, 102 (4), 1191-1199.)

Not unexpectedly, most investigated nNOS inhibitors are mimetics of arginine and act as competitive inhibitors. One major challenge in designing nNOS inhibitors is that eNOS and iNOS share high sequence similarity and an identical overall architecture with nNOS, especially in their substrate-binding sites. Lack of isoform selectivity could have deleterious effects; inhibition of eNOS can cause severe hypertension, and iNOS inhibition could impair immune system activation. Previously, fragment hopping and subsequent structure-based optimization afforded compounds 1 and 2 (representative nNOS inhibitors are shown in FIG. 1). These compounds are highly potent and selective nNOS inhibitors, and compound 1 reverses a hypoxic-ischemic brain damage phenotype in newborn rabbit kits when administered intravenously to the dam. (See, Ji, H.; Tan, S.; Igarashi, J.; Li, H.; Derrick, M.; Martásek, P.; Roman, L. J.; Vasquez-Vivar, J.; Poulos, T. L.; and Silverman, R. B. Selective Neuronal Nitric Oxide Synthase Inhibitors and the Prevention of Cerebral Palsy. *Ann. Neurol.* 2009. 65, 209-217.)

Although effective, compounds 1 and 2 suffer from several drawbacks. Like most arginine mimics, they are very polar and hydrophilic and contain numerous basic moieties and hydrogen-bond donors, as well as many rotatable bonds and a high total polar surface area (tPSA), all properties that hamper both GI absorption and blood-brain barrier permeation. Many attempts to improve the bioavailability of these compounds have been made, including alkylation, fluorination, introduction of lipophilic tails, and replacement of amine moieties—most of these strategies either diminished potency or selectivity or were synthetically challenging. The chiral scaffolds of 1 and 2 are also difficult (>12 steps) to prepare, making them less desirable, from a clinical standpoint, than simpler scaffolds such as that of a compound 3 and commercial candidate 4; (potencies and selectivities given in FIG. 1). Nonetheless, these simplified molecules are not without fault; their isoform selectivities are lower, 3 suffers from poor Caco-2 permeability, and 4 is much less potent in cell-based assays than against isolated enzymes—both likely the result, in part, of the amidine moiety, which will be charged at physiological pH.

Accordingly, the design of NOS inhibitors remains an on-going concern in the art. In particular, the search continues for compounds providing good bioavailability without compromising potency and/or selectivity, while offering the advantages and benefits associated with ease of preparation and molecular variation.

SUMMARY OF THE INVENTION

In light of the foregoing, it is an object of the present invention to provide selective nNOS inhibitor compounds and/or methods for their use, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all of its respects, to every aspect of this invention. As such, the following objects can be viewed in the alternative with respect to any one aspect of this invention.

It can be an object of the present invention to provide compounds which, in comparison with the prior art, can be prepared using relatively simple, straight-forward synthetic techniques with inexpensive and/or commercially-available starting materials.

It can also be an object of the present invention to provide such compounds exhibiting improved oral bioavailability and blood-brain barrier penetration.

It can be another object of the present invention, alone or in conjunction with one or more of the preceding objectives, to provide a structural scaffold for the development of a range of compounds for selective inhibition of nNOS.

Other objects, features, benefits and advantages of the present invention will be apparent from the summary and the following descriptions of certain embodiments and will be readily apparent to those skilled in the art having knowledge of synthetic techniques of the sort described herein. Such objects, features, benefits and advantages will be apparent from the above as taken into conjunction with the accompanying examples, data, figures and all reasonable inferences to be drawn therefrom alone or with consideration of the references incorporated herein.

In part, the present invention can be directed to compounds of a formula

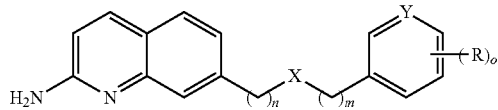

wherein X can be selected from O and NH; Y can be selected from CH and N; n can be an integer selected from 1-2; m can be an integer selected from 0-3; o can be an integer selected from 0-2; and each R can be independently selected from halo, cyano, alkyl, alkoxy, amino, alkylamino, aminealkyl and N-substituted and oxa-substituted (—O—) aminealkyl moieties, and salts thereof. Independent of the foregoing, and as illustrated below, such a quinoline moiety can be substituted at either the 6-position or 7-position (as shown above), with a linking moiety of the sort described above.

In certain embodiments, as discussed above, X can be NH and Y can be CH. In certain such embodiments, n can be 1, and m can be 0-1. Alternatively, X can be NH and Y can be N; and, in certain such embodiments, m can be 3. Regardless, R can be selected from fluoro, cyano, methoxy, N-methylamino, N,N-dimethylamino, alkyl, aminealkyl, and N-methyl- and N,N-dimethylaminealkyl moieties.

In certain other embodiments, X can be O and Y can be CH. In certain such embodiments, n can be 1, m can be 0, and R can be selected from one or a combination of moieties of the sort discussed above or elsewhere herein. Alternatively, Y can be NH and, without limitation, o can be 1 and R can be an N-methylaminealkyl moiety.

In part, the present invention can also be directed to compounds of a formula

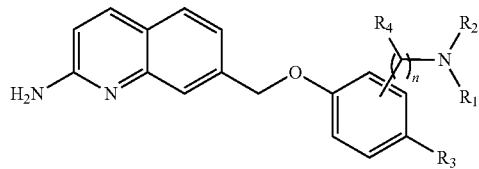

wherein, $R_1$ and $R_2$ can be independently selected from H and methyl moieties; $R_3$ can be selected from R moieties of the sort discussed above and illustrated elsewhere herein (e.g., without limitation halo, cyano, etc.); n can be an integer selected from 0-3; and each $R_4$ can be independently selected from H and methyl moieties, and salts thereof.

In part, the present invention can also be directed to compounds of a formula

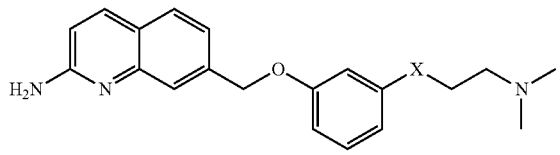

wherein X can be selected from CH and O (e.g., without limitation, providing an oxa-substituted N,N-dimethylaminealkyl moiety), and salts thereof.

In part, the present invention can be directed to compounds of a formula

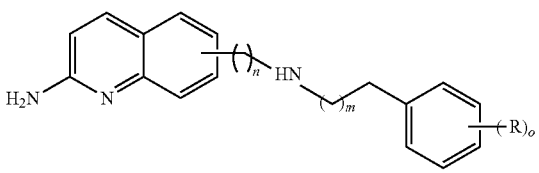

wherein n can be an integer selected from 1-2; m can be an integer selected from 0-2; R can be selected from fluoro and chloro groups and combinations thereof; and o can be an integer selected from 0-2, and salts thereof. In certain embodiments, m can be 1 or 2. In certain such embodiments, the sum of n and m can be 4. Regardless, in certain embodiments, o can be 1 and R can be F, optionally with a meta-relationship to the alkyleneamine linker moiety. Independent of the foregoing and other structural considerations, such a quinoline moiety can be substituted at either the 6- or 7-positions thereof with such an arylalkyleneaminealkylene moiety.

Accordingly, in part, the present invention can be directed to compounds of a formula

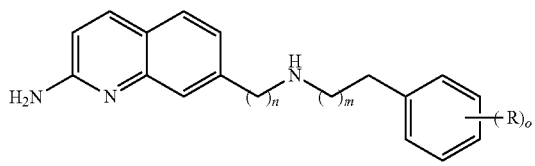

and salts thereof, wherein n, m, o and R can be as described above or illustrated elsewhere herein.

Alternatively, in part, the present invention can be directed to compounds of a formula

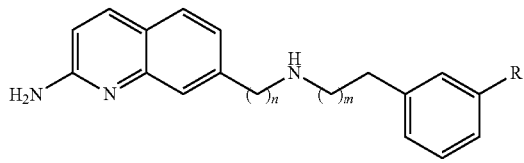

wherein n can be an integer selected from 1-2; m can be an integer selected from 2-3, providing where m is 3, n is 1; and R can be selected from chloro and fluoro groups, and salts thereof. In certain embodiments, the sum of n and m can be 4. Regardless, R can be fluoro.

It will be understood by those skilled in the art that compounds of this invention can comprise an acid salt, hydrate and/or solvate of any such compound. Without limitation, certain embodiments can be partially or fully protonated, comprising a primary, secondary and/or tertiary amine, whereby the counter ion(s) of such an ammonium salt can be a conjugate base of a protic acid. Further, as may pertain to certain embodiments, the present compounds are without stereochemical limitation. Where such compounds and/or their intermediates are available as racemic mixtures, the respective isomers can be resolved. Likewise, where such compounds are diastereomers, the corresponding enantiomers can be separated. Accordingly, any such stereocenter can be (S) or (R) with respect to any other stereocenter(s), whether such a compound is present as a salt, hydrate and/or solvate. Regardless, any such compound(s) can be provided as part of a pharmaceutical composition comprising a pharmaceutically-acceptable carrier component for use in conjunction with a method or medicament of this invention.

In part, the present invention can also be directed to a method of affecting, inhibiting and/or otherwise modulating nitric oxide synthase activity. Such a method can comprise contacting, whether in vitro or in vivo, a nitric oxide synthase with an effective amount of any one or more of the present compounds or compositions, including but not limited to those compounds illustrated or inferred by the following examples, figures, accompanying synthetic schemes and/or incorporated references. More specifically, as discussed below, the present invention can provide a method for selective inhibition of neuronal nitric oxide synthase. Regardless, such methods can comprise providing a compound or corresponding pharmaceutical composition of this invention; and contacting a nitric oxide synthase with such a compound/composition. In certain embodiments, as demonstrated below, such contact or administration can selectively inhibit neuronal nitric oxide synthase over inducible and endothelial isoforms.

DETAILED DESCRIPTION OF CERTAIN EMBODIMENTS

Figure 1:
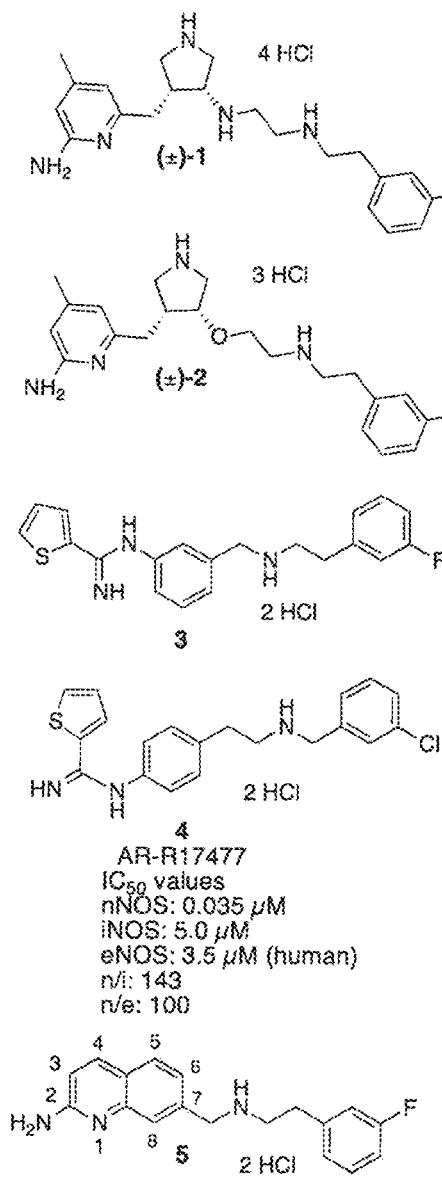
FIG. 1. Prior art compounds 1-4 and a representative nNOS inhibitor compound 5 discussed in this study. Chemical properties were calculated using ChemBioDraw version 12.3.

As relates to certain non-limiting embodiments of this invention, the generation of more structurally-simple and synthetically-available nNOS inhibitor scaffolds was undertaken, in one respect, to replace the amidine group of prior art molecule 3. For suitable amidine replacement, such a group should be stable, weakly basic (e.g., pKa between 6 and 8) and possess as few hydrogen-bond donors as possible. One such moiety is the 2-aminoquinoline group, with a $pK_a$ of 7.3, and a considerably higher CLogP than the amino-pyridine group of prior art compounds 1 and 2. With such considerations, aminoquinoline compound 5 was prepared.

Assaying compound 5 against purified nNOS, eNOS, and iNOS revealed potent inhibition of nNOS (74 nM) and good selectivity for nNOS over iNOS, but the selectivity for nNOS over eNOS was only approximately 6-fold. There is a hydrophobic pocket at the far end of the substrate access channel of nNOS; contact between an inhibitor and the residues lining this pocket is implicated in high selectivity for nNOS over the other two isoforms. In the case of 5, it was hypothesized that the low selectivity resulted from the lack of contact between residues in this pocket and the fluorophenyl ring. Preliminary docking studies and crystallography indicated that elongation of the chain between the aminoquinoline system and the distal fluorophenyl ring, moving the position of the secondary amine, or a combination of both, might provide the right length and orientation to reach this hydrophobic pocket, and a series of analogues investigating chain length (6-9) and nitrogen position was, therefore, prepared. Additionally, on the basis of computer modeling, it was hypothesized that placement of the "tail" of the inhibitor at position 6 of the aminoquinoline system (instead of position 7) could also be effective; to this end, compounds 10-13 were prepared. Finally, it was thought that the use of other halogens and substitution patterns on the non-coordinating aryl ring could be beneficial for enhancing potency and selectivity, so a small series of 7-substituted compounds (14-16) with different halogens and substitution patterns was prepared. All compounds were assayed against purified rat nNOS, and select compounds were assayed against eNOS, iNOS, and human nNOS, and for cellular permeability in a Caco-2 model.

6- and 7-Substituted 2-aminoquinolines were prepared by variations of methods reported in the literature. In the present study, 7-substituted aminoquinolines (5-9 and 14-16) were prepared by a versatile, late-divergent route that began with the preparation of 3'-methylcinnamanilide (17) from m-toluidine and cinnamoyl chloride, by literature procedures. Compound 17 was subsequently treated with an excess of aluminum chloride in chlorobenzene to affect cyclization (with concomitant cleavage of the C-aryl bond) to yield the carbostyril 18 as a mixture of the 7-isomer 18a (major) and 5-isomer 18b (minor). The isomers were not separated at this stage, but were converted into the 2-chloroquinolines 19a and 19b by treatment with $POCl_3$; unwanted 5-isomer 19b was removed by fractional crystallization from isopropanol. Pure 19a was converted into 2-acetamidoquinoline 20, and free-radical bromination afforded versatile intermediate 21 (Scheme 1).

Scheme 1[a]

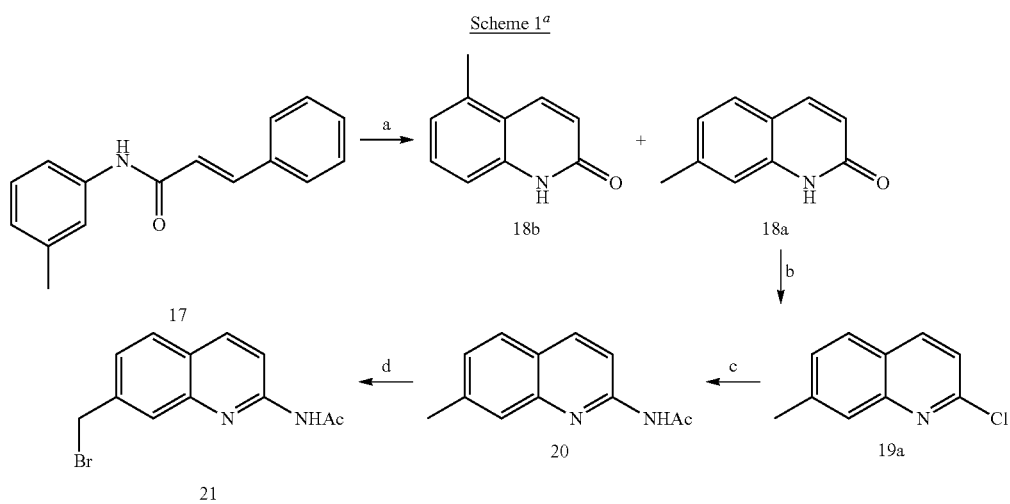

[a]Reagents and conditions: (a) AlCl₃, PhCl, 90° C.; (b) i. POCl₃, reflux, ii. fractional crystallization from i-PrOH after isolation; (c) AcNH₂, K₂CO₃, reflux (~230° C.); (d) NBS, (PhCO₂)₂, benzene, reflux.

For those aminoquinoline analogues possessing one methylene unit between the quinoline system and the secondary amine (5 and 9, Schemes 2 and 3) the bromide was treated with a slight excess of 3-fluorophenethylamine (22) or 3-fluoro-1-phenylpropanamine (25, prepared by hydrogenation of 3-fluorophenethyl cyanide [24, prepared from 23]) under basic $S_N2$ conditions, to afford amines 26 and 27, respectively (the former was characterized, while the latter was simply carried on to the last step). Deacetylation of these compounds in refluxing methanolic K₂CO₃ afforded the final analogues as their syrupy free-bases, which were readily converted to water-soluble dihydrochloride salts 5 and 9 by treatment with methanolic HCl.

Scheme 2[a]

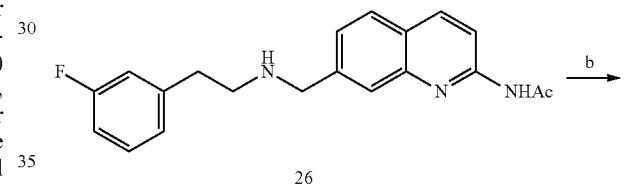

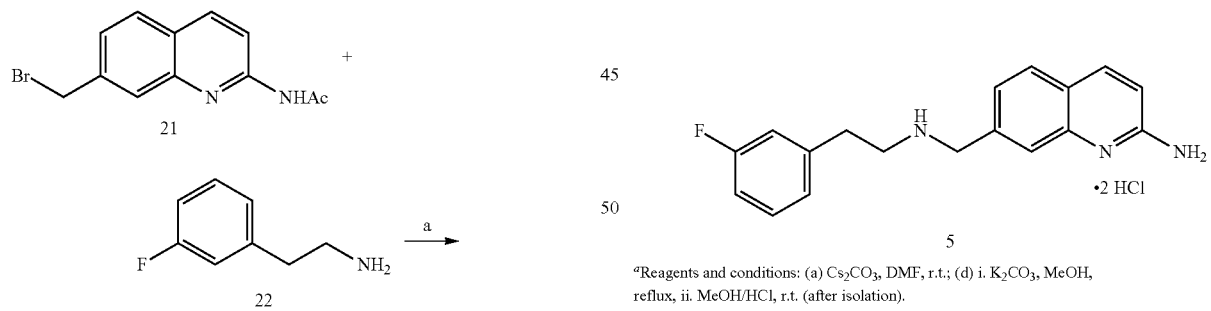

[a]Reagents and conditions: (a) Cs₂CO₃, DMF, r.t.; (d) i. K₂CO₃, MeOH, reflux, ii. MeOH/HCl, r.t. (after isolation).

Scheme 3[a]

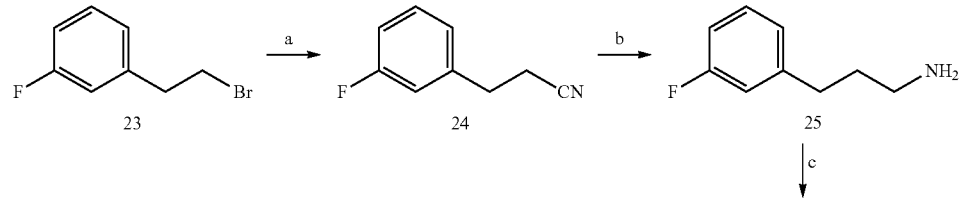

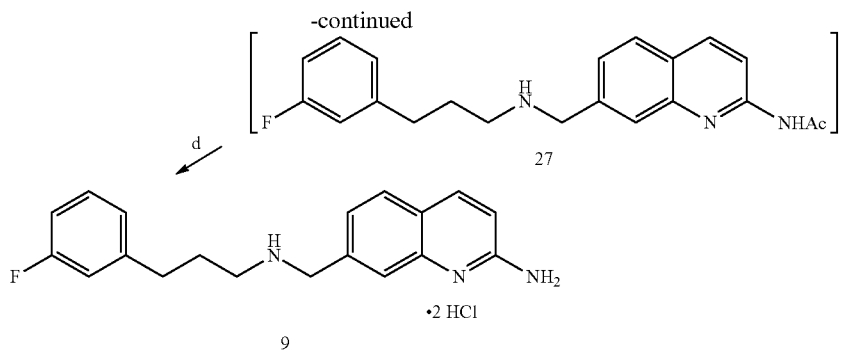

*Reagents and conditions: (a) NaCN, DMF, 60° C.; (b) H₂, Raney Ni, NH₃/MeOH/EtOH, r.t.; (c) 21, Cs₂CO₃, DMF, r.t.; (d) i. K₂CO₃, MeOH, reflux, ii. MeOH/HCl, r.t. (after isolation).

Various other compounds of this invention can be prepared, analogously. For instance, reaction of bromide 21, with a substituted aniline, phenylmethylamine, phenyethylamine or an unsubstituted pyridinylpropylamine compound, under basic substitution conditions, can afford the corresponding N-linked compounds. (See, e.g., the representative compounds of FIG. 2.)

Aminoquinolines possessing two methylene units between the quinoline system and secondary amine (6, 7, 8, and 14-16) were likewise prepared from bromide 21 by homologation with cyanide ion to afford nitrile 28. (See, Scheme 4, below.) This compound was reduced to a very polar quinolinyl-ethanamine (29) using hydrogen and Raney nickel in an ethanol/methanolic ammonia solution; 29 was used crude in the next step (confirmed by TLC and MS). Benzyl analogue 6 was prepared by an "indirect" reductive amination, where 29 was treated with 3-fluorobenzaldehyde (30) under mildly acidic, dehydrating conditions. When the aldehyde was consumed (as measured by TLC), the dehydrating agent was filtered, and the resulting aldimine was reduced by NaBH₄. Subsequent deacetylation, workup, and acidification afforded 6.

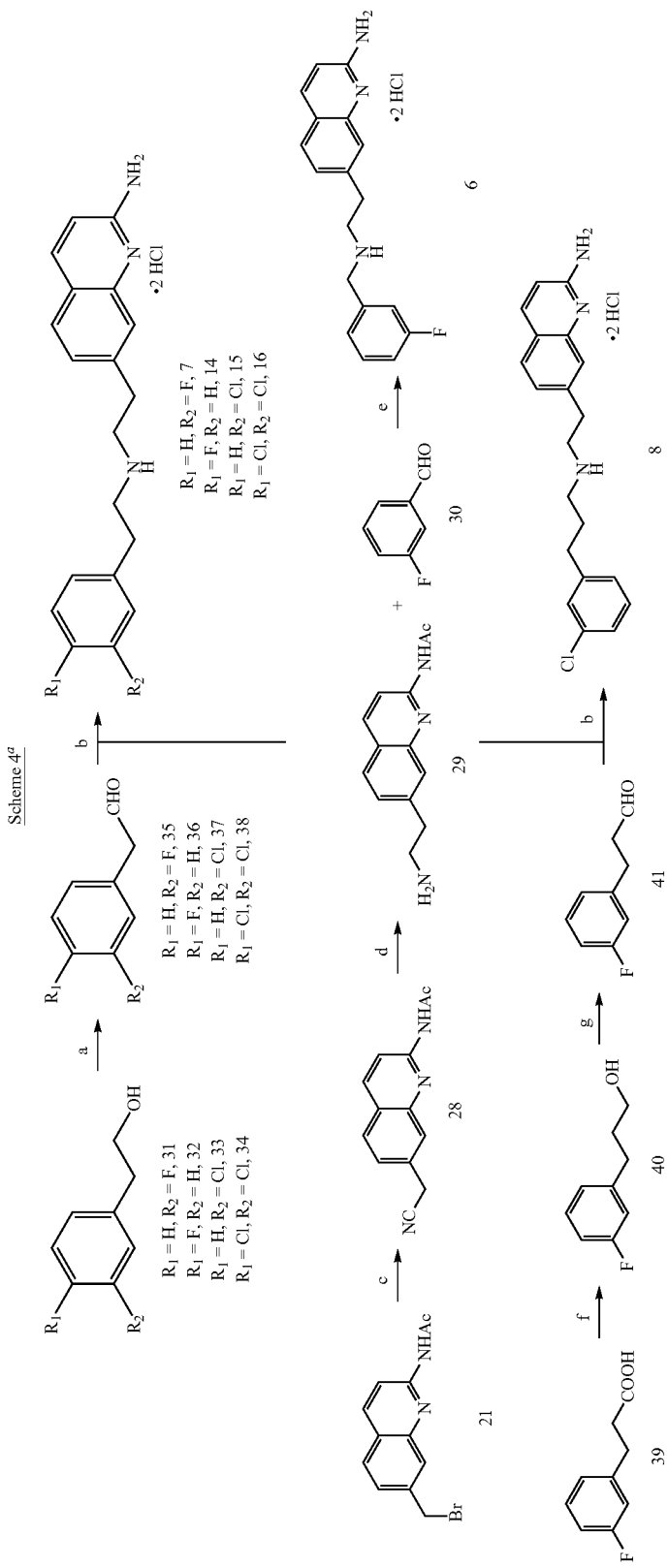

To prepare phenethyl analogues 7, 14, 15, and 16 (Scheme 4), requisite phenylacetaldehydes 35-38 were prepared by Dess-Martin oxidation of commercially available phenethyl alcohols 31-34, respectively. A "direct" reductive amination using 29, the desired aldehyde, sodium triacetoxyborohydride, MgSO$_4$, and catalytic AcOH was used to assemble the cores of the final analogues. Yields were low because of dialkylation and aldehyde condensation by-products; the use of other solvents, dehydrating agents, and reductants failed to alleviate these problems; the aldehydes may be light- and acid-sensitive as well. For these analogues, the intermediate acetamides were not characterized after isolation, but were immediately deprotected (because of some concerns about their stability) to yield 7, 14, 15, and 16, and converted into dihydrochloride salts, which could be easily purified by crystallization, trituration, or preparative HPLC. Finally, the preparation of propyl analogue 8 began with 3-fluorophenylpropionic acid (39). Reduction to phenylpropanol 40, followed by Swern oxidation, afforded sensitive aldehyde 41. Reductive amination using amine 29, deacetylation, workup, and acidification afforded 8.

6-Substituted 2-aminoquinolines were prepared by a similar means to those described above, beginning instead with 4'-methylcinnamanilide (42, Scheme 5). Using the cyclization-dearylation procedure, 43 was prepared and immediately chlorinated (to 44) using POCl$_3$. Amidation (to yield 45) and bromination afforded 46. Compound 46 was treated with 22, and the resulting acetamide was deacetylated, isolated, and acidified as before to yield 10.

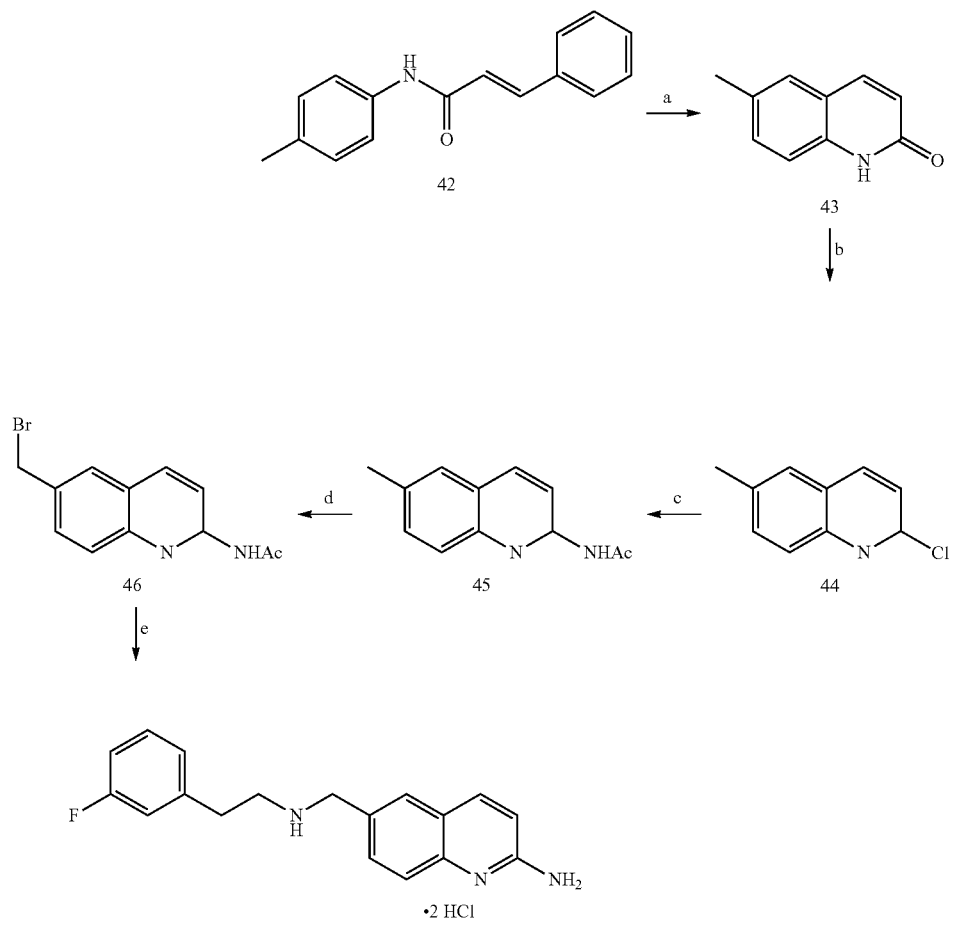

Scheme 5$^a$ $^a$Reagents and conditions: (a) AlCl$_3$, PhCl, 90° C.; (b) POCl$_3$, reflux; (c) AcNH$_2$, K$_2$CO$_3$, reflux (~230° C.); (d) NBS, (PhCO$_2$)$_2$, benzene, reflux; (e) i. 22, Cs$_2$CO$_3$, DMF, r.t., ii. K$_2$CO$_3$, MeOH, reflux (after isolation), iii. MeOH, HCl, r.t. (after isolation).

Likewise, homologation of 46 with cyanide ion afforded 47, which was readily reduced to ethanamine 48 (see, Scheme 6; confirmed by TLC, MS and $^1$H-NMR). The indirect reductive amination procedure (using 30) afforded 11 after deacetylation, isolation, and acidification. The direct reductive amination employing Na(OAc)$_3$BH (with aldehyde 35) similarly afforded 12 after deacetylation/acidification, while the same procedure using 41 instead yielded 13 after deprotection and salt formation.

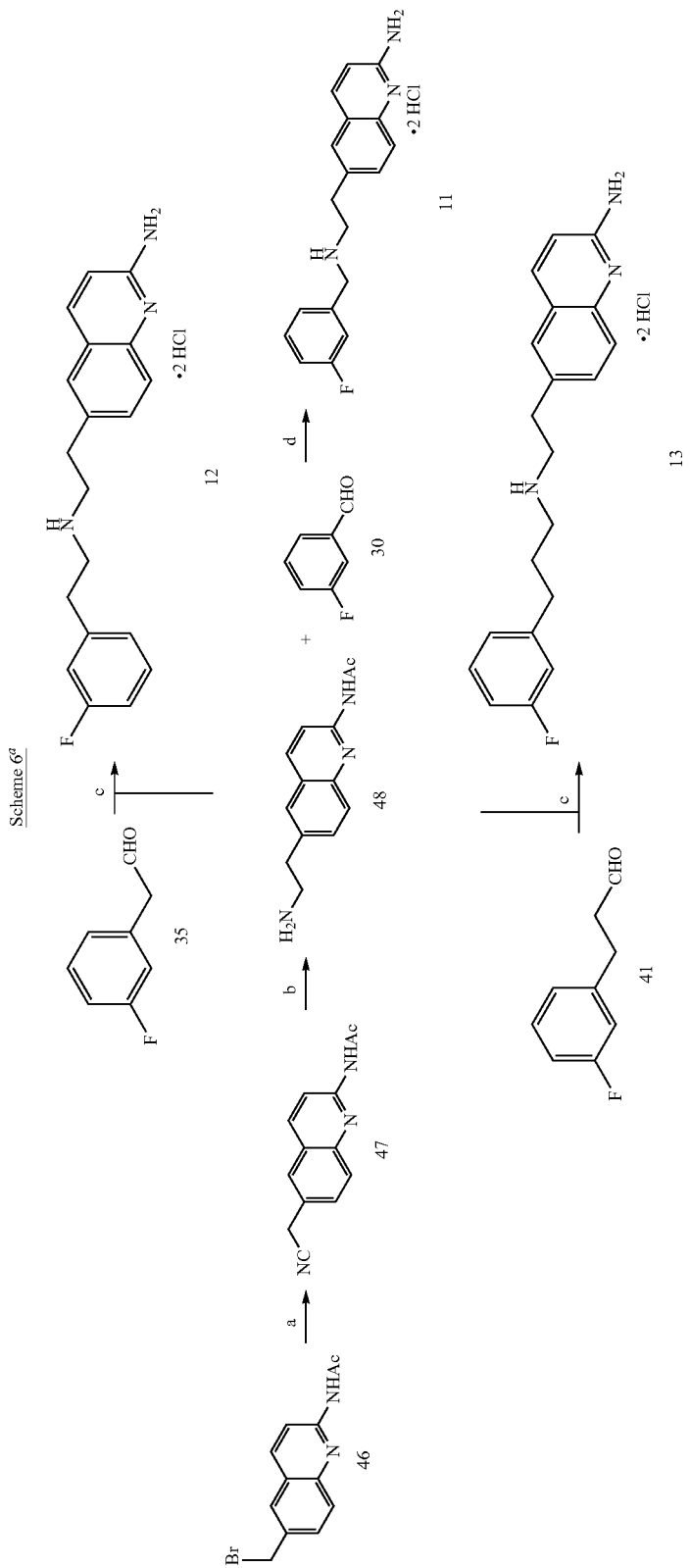
Scheme 6[a]
[a]Reagents and conditions: (a) NaCN, DMF, r.t.; (b) H₂, Raney Ni, NH₃/MeOH/EtOH, r.t.; (c) i. AcOH, MgSO₄, CHCl₃/MeOH, r.t.-0°C., ii. Na(OAc)₃BH, 0°C.-r.t., iii. K₂CO₃, MeOH, reflux (after isolation), iv. HCl, MeOH, r.t. (after isolation), (d) i. AcOH, Na₂SO₄, CHCl₃/MeOH, r.t., ii. NaBH₄, MeOH, r.t., iii. K₂CO₃, MeOH, reflux (after isolation), iv. HCl, MeOH, r.t. (after isolation)

Figure 3:
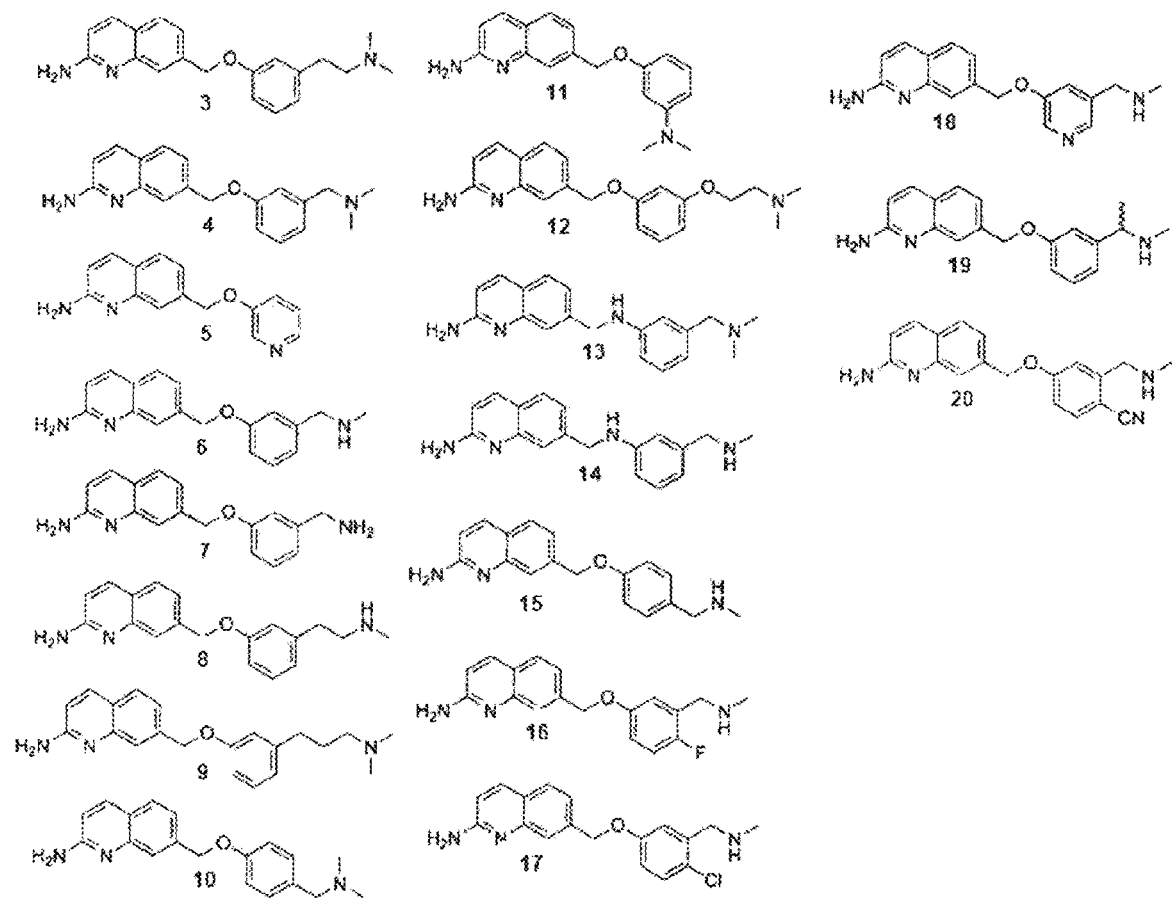

Representative O-linked compounds are illustrated in FIG. 3 and prepared as provided with reference to Schemes 7-14. As discussed above, 7-substituted-2-aminoquinolines were prepared via the readily accessible chloroquinoline 19a, by performing a Koródi amidation (treatment with an excess of $K_2CO_3$ in neat acetamide at reflux to produce the 2-acetamidoquinoline 20). As an alternative approach (Scheme 7), amination of 2-chloroquinolines was achieved using LHMDS as both an ammonia surrogate and base; applying this procedure to 24 afforded the 2-aminoquinoline 25 in nearly quantitative yields, even on multigram scale. Treatment with N-acetylimidazole in refluxing THF afforded 26, and free-radical bromination, as previously reported, yielded the versatile bromide 27. (Notwithstanding the foregoing Schemes 1-6, Examples 1-30 and FIG. 1, Schemes 7-13 and FIG. 3 employ independent numerical references for the respective aminoquinoline compounds and corresponding intermediate and starting materials.)

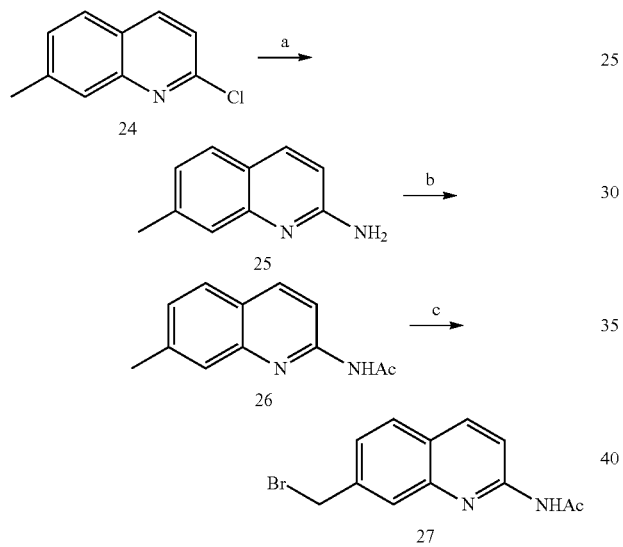

[a]Reagents and conditions: (a) LHMDS, Pd$_2$(dba)$_3$, DavePhos, THF/dioxane, 100° C.; (b) N-acetylimidazole, THF, reflux; (c) NBS, (PhCO$_2$)$_2$, benzene, reflux.

Figure 2:
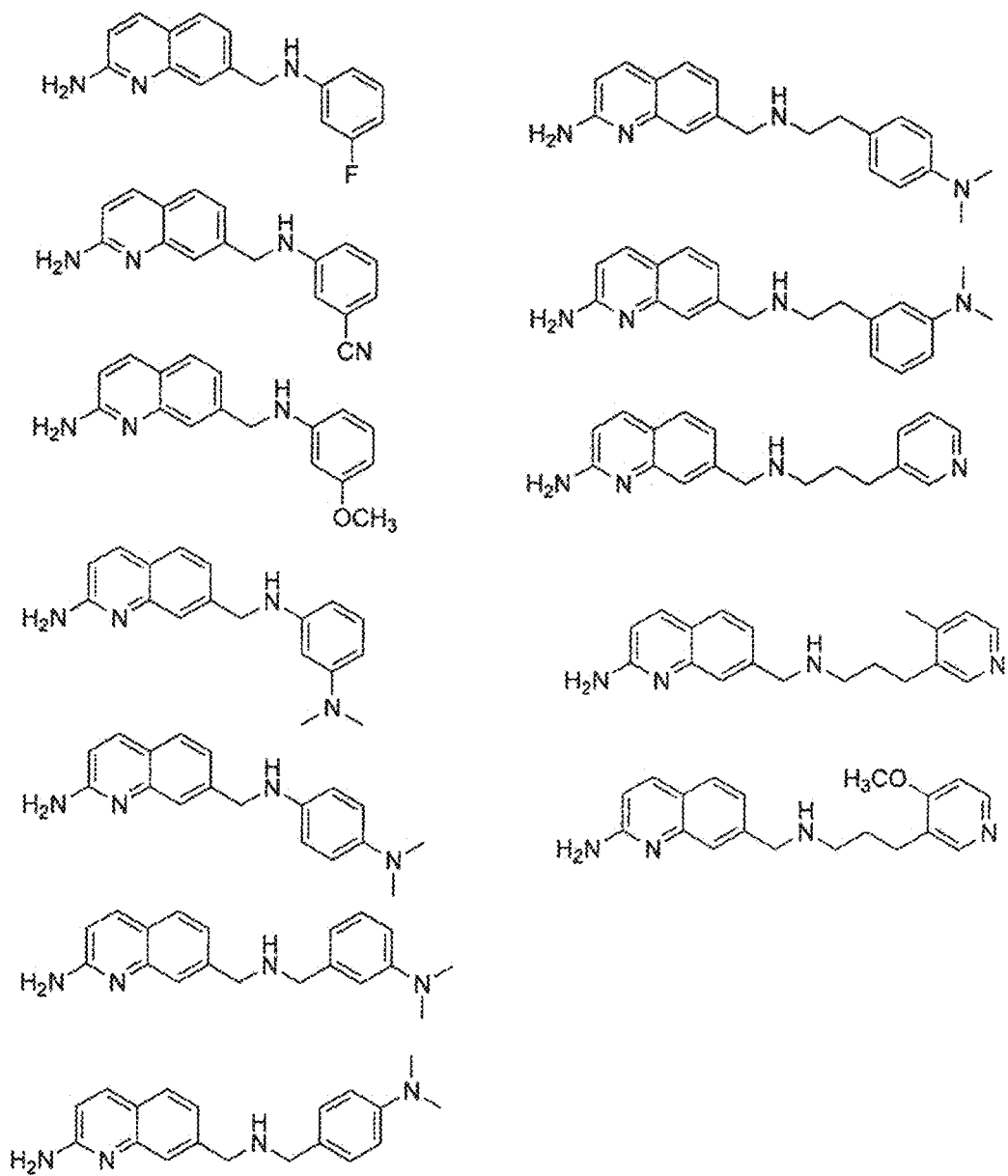
FIGS. 2-3. Chemical structures of representative compounds of this invention, in accordance with various non-limiting embodiments thereof.

With bromide 27 in hand, the phenol (and aniline) intermediate materials were then prepared prior to the final assembly of the corresponding phenyl ether or aniline compounds (FIGS. 2-3). To prepare phenyl ether 3 (Scheme 8A), 3-methoxyphenethylamine (28) was dimethylated, and the methyl group of 29 was removed to yield phenol 30. The monomethylated phenol 33 (for compound 8) was prepared from 3-methoxyphenethyl bromide (31, Scheme 8B) and excess methylamine solution, followed by demethylation of 32 and immediate Boc-protection, to aid in purification and prevent later interference by the free secondary amine. For the benzylic amine of compound 4, the phenol 35 (Scheme 8C) was prepared by reductive amination of commercially available 3-hydroxybenzaldehyde 34 with N,N-dimethylamine. Similarly, exchanging N,N-dimethylamine for methylamine (as needed for compound 6) yielded the an amine, which was immediately Boc-protected as 36. Phenol 38 (Scheme 8D) was prepared for the synthesis of compound 7 by Boc-protecting 3-hydroxybenzylamine (37).

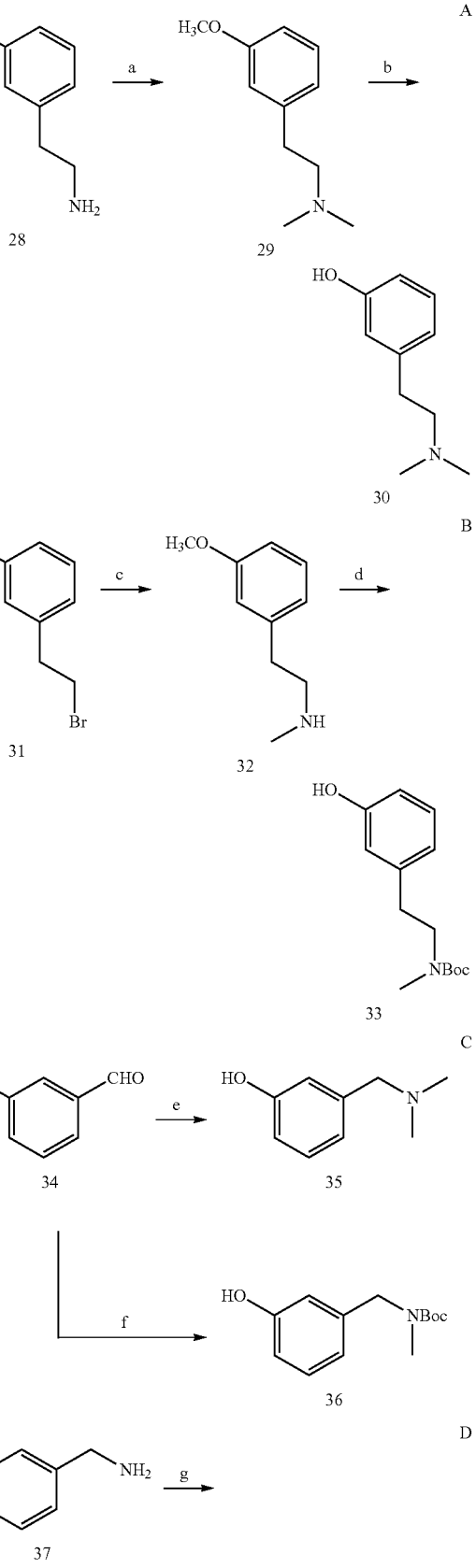

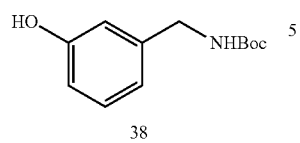

*Reagents and conditions: (a) formalin, formic acid, DMF, 0° C.-120° C., 5 h; (b) 48% HBr, AcOH, reflux; (c) 40% MeNH$_2$ in H$_2$O, THF/H$_2$O, r.t.; (d) i. 48% HBr, HOAc, reflux, ii. Boc$_2$O, Et$_3$N, THF, r.t.; (e) i. Me$_2$NH-HCl, Et$_3$N, CHCl$_3$/MeOH, Na$_2$SO$_4$, r.t.; ii. Na(OAc)$_3$BH, r.t.; (f) i. MeNH$_2$ in THF, cat. AcOH, CHCl$_3$/MeOH, Na$_2$SO$_4$, r.t.; ii. NaBH$_4$, MeOH, 0° C.-r.t., iii. Boc$_2$O, THF, r.t.; (g) Boc$_2$O, THF, 0° C.-r.t.

With reference to Scheme 9, the longer linker of 9, via phenol 41, was prepared by the Sonogashira coupling of 3-iodophenol (39) with N,N-dimethylpropargylamine, followed by reduction of the triple bond of 40 (Scheme 9A). For compound 12, the intermediate 43 was prepared by a Mitsunobu reaction between resorcinol (42) and 3-(N,N-dimethylamino)ethanol (Scheme 9B). With reference to Scheme 10, as performed for the meta-analogues, the intermediate phenols 45 and 46 (for para-analogues 10 and 15, respectively) were prepared from 4-hydroxybenzaldehyde (44), and either methylamine (for 46) or N,N-dimethylamine (for 45).

Scheme 9$^a$

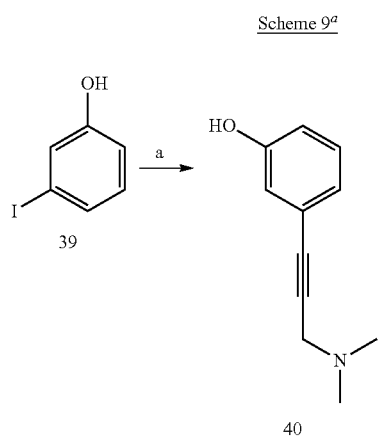

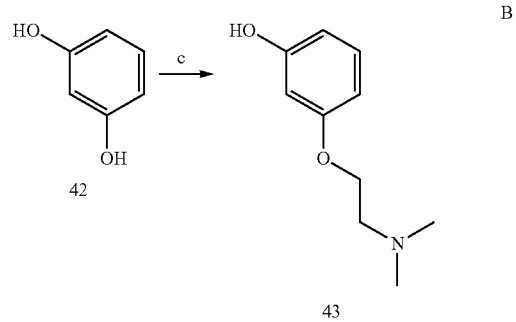

*Reagents and conditions: (a) (a) CuI (10 mol %), [(PPh$_3$)$_3$]$_4$Pd (5 mol %), THF/Et$_3$N, r.t.; (b) H$_2$, Pd/C, MeOH, r.t.; (c) PPh$_3$, DEAD, THF, 0° C.; r.t.

Scheme 10$^a$

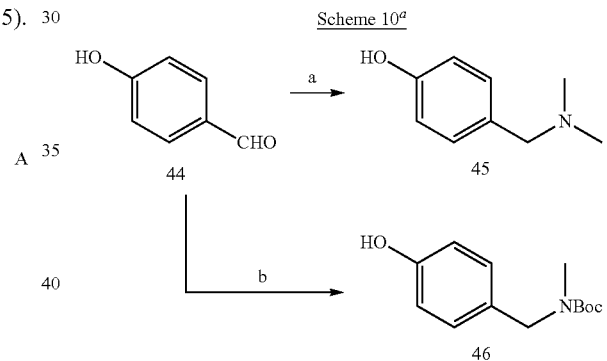

*Reagents and conditions: (a) i. Me$_2$NH-HCl, Et$_3$N, Na$_2$SO$_4$, CHCl$_3$/MeOH, r.t.; ii. Na(OAc)$_3$BH, r.t. (b) i. MeNH$_2$ in THF, CHCl$_3$/MeOH, Na$_2$SO$_4$, AcOH, r.t.; ii. NaBH$_4$, MeOH, 0° C.-r.t., iii. Boc$_2$O, THF, r.t.

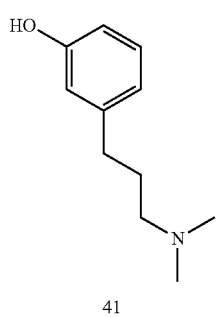

With reference to Scheme 11, the aniline materials for preparation of compounds 13 and 14 were both prepared from 3-nitrobenzyl bromide (47) upon treatment with either dimethylamine (48) or methylamine (followed by Boc-protection to yield 50). Reduction of the nitro group with Raney nickel afforded 49 (for 13) and 51 (for 14).

Scheme 11[a]

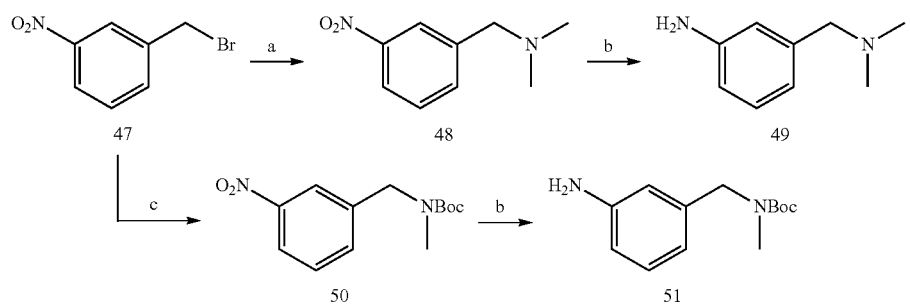

[a]Reagents and conditions: (a) Me$_2$NH—HCl, Et$_3$N, CH$_2$Cl$_2$ and MeOH, r.t.; (b) H$_2$, Raney Ni, MeOH, r.t.; (c) i. MeNH$_2$ in THF, CH$_2$Cl$_2$, r.t., ii. Boc$_2$O, CH$_2$Cl$_2$, r.t.

With reference to Scheme 12A, the substituted phenols (for compounds 16-17 and 19-20) can be prepared by employing reductive amination/Boc protection to commercially available aldehydes (52, 53) or acetophenones (54) to yield protected amines 56-58. To prepare cyanophenol 60 (for compound 20), the brominated precursor phenol 59 (prepared from 55) was subjected to a palladium-catalyzed cyanation. Lastly, the pyridinol 63 (for compound 18, Scheme 12B) was prepared by reductive amination of nicotinaldehyde 61, and cleavage of the methyl group and protection furnished 63.

Scheme 12[a]

A

R$_1$ = H, R$_2$ = F, 52
R$_1$ = H, R$_2$ = Cl, 53
R$_1$ = CH$_3$, R$_2$ = H, 54
R$_1$ = H, R$_2$ = Br, 55

R$_1$ = H, R$_2$ = F, 56
R$_1$ = H, R$_2$ = Cl, 57
R$_1$ = CH$_3$, R$_2$ = H, 58
R$_1$ = H, R$_2$ = Br, 59
R$_1$ = H, R$_2$ = CN, 60

B

61 → 62

-continued

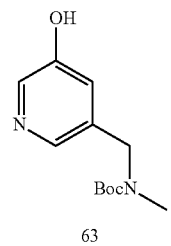

63

[a]Reagents and conditions: (a) i. MeNH$_2$ in THF, cat. AcOH, CHCl$_3$/MeOH, NaSO$_4$, r.t.; ii. NaBH$_4$, MeOH, 0° C.-r.t., iii. Boc$_2$O, THF, r.t.; (b) ZnCN$_2$, Pd(OAc)$_2$, PPh$_3$, DMF, 100° C.; (c) i. HBr/H$_2$O, HOAc, 130° C.; ii. Et$_3$N, Boc$_2$O, THF/MeOH, r.t.

With the components of the phenyl ether-substituted quinolines in hand, assembly of the final compounds of FIG. 3 (Scheme 13) was completed by first treating the desired phenol (30, 33, 35, 36, 38, 41, 43, 45, 46, 56-58, 60, 63, or commercially available 3-hydroxypyridine or 3-(N,N-dimethylamino)phenol, in the case of compounds 5 and 18, respectively) with sodium hydride in DMF at 0° C. A solution of 27 was then added, and the reaction was typically complete within 1 h. The intermediate acetamides (64-79) were not characterized and were purified and deprotected immediately: the acetyl group was first removed by K$_2$CO$_3$ in refluxing methanol, and after isolation, the free aminoquinolines were treated with methanolic HCl in ether to produce water-soluble hydrochloride salts. Compounds without a Boc group present were isolated after 5-15 min; those with a Boc group were stirred overnight to ensure complete deprotection. In the case of 76, HCl induced unfavorable side-reactions, so TFA was instead used for deprotection.

Scheme 13[a]

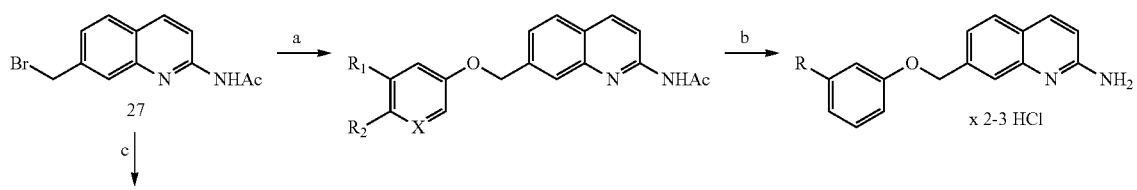

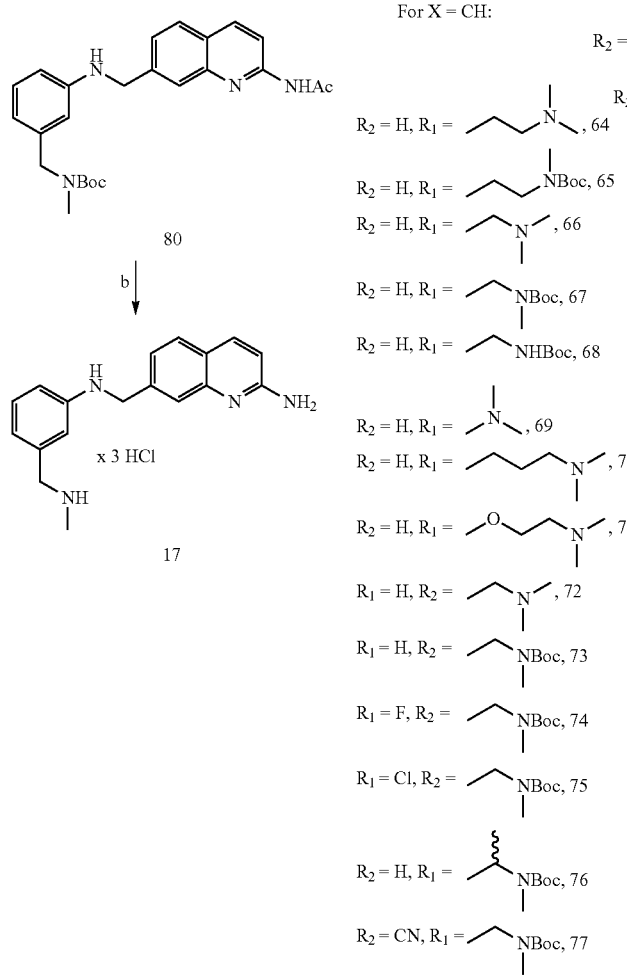

*aReagents and conditions: (a) i. Phenols 30, 33, 35, 36, 38, 41, 43, 45, 46, 56-58, 60, 63, 3-(N,N-dimethylamino)phenol, or 3-hydroxypyridine, NaH, DMF, 0° C., ii. 27 (in DMF), 0° C.; (b) i. K₂CO₃, MeOH, reflux, ii, HCl/MeOH, ether, r.t., or TFA/DCM (for 76), after isolation, 5 min-overnight.; (c) 51 (2.5 eq.), cat. KI, μwave, MeCN, 110° C.

The microwave alkylation procedure of Romero et al. was employed to synthesize the aniline 17 (Scheme 13) Compound 27, excess 51, and catalytic potassium iodide were heated in acetonitrile under microwave radiation to furnish intermediate 80, which was deprotected as described above. However, the low acidity and reactivity of aniline 49 produced only water-soluble quaternization by-products upon reaction with 27. It was proposed that the two halves of the N-linked compound 13 could be joined via reductive amination as previously reported, beginning with the quinolinecarboxaldehyde 86 (Scheme 14). After unsuccessful attempts to prepare 86 from 26 and 27, the aldehyde was prepared in five steps (Scheme 14), starting with a Wittig cyanovinylation of commercially available aldehyde 81. The desired trans-isomer 82 was obtained in 80% yield and was readily purified. Reductive cyclization in the presence of iron yielded aminoquinoline 83; and acetylation of the non-nucleophilic amine proceeded in good yield using N-acetylimidazole. Ester 84 was reduced to alcohol 85, and the oxidation to 86 was performed using Dess-Martin periodinane. An indirect reductive amination with 49 was effective at elevated temperatures, and the crude acetamide was deprotected to yield final compound 13 in low yield but very high purity.

Scheme 14ª

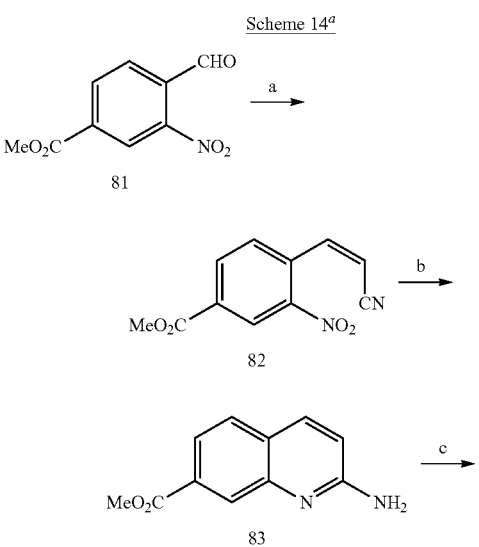

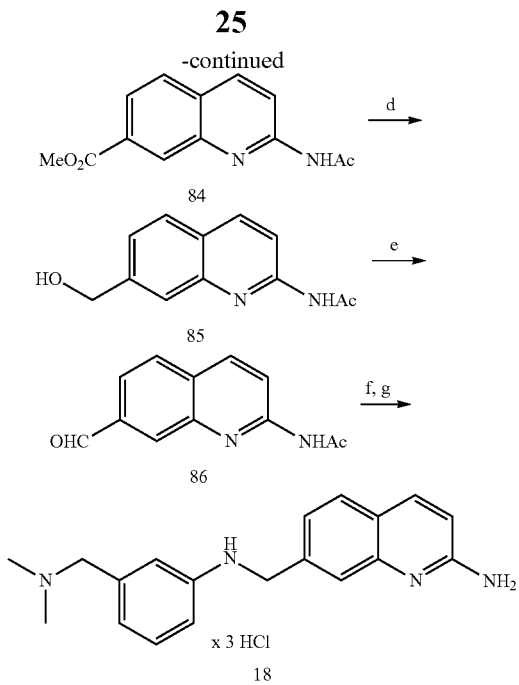

[a]Reagents and conditions: (a)(Triphenylphosphoranylidene)acetonitrile (slow addition), CH₂Cl₂, -10° C.; (b) Fe powder, DMF/AcOH, 100° C.; (c) N-acetylimidazole, cat. DMAP, dioxane, 100° C.; (d) LiAlH₄ 1.5 eq.), THF, -10° C.-0° C.; (e) PPh₃, CBr₄, THF, 0° C.-r.t.; (e) Dess-Martin periodinane, CH₂Cl₂, r.t.; (f) i. EtOH, AcOH, Na₂SO₄, 60° C., ii., NaBH₄, r.t., (g) i. K₂CO₃, MeOH, reflux; ii. HCl/MeOH, ether, r.t. (after isolation).

Compounds 5-16 were assayed against purified rat nNOS, bovine eNOS, and murine macrophage iNOS (there is large active-site homology among species), using the hemoglobin capture assay, as previously described. (Labby, K. J.; Xue, F.; Kraus, J. M.; Ji, H.; Mataka, J.; Li, H.; Martásek, P.; Roman, L. J.; Poulos, T. L.; and Silverman, R. B. Intramolecular hydrogen bonding: A potential strategy for more bioavailable inhibitors of neuronal nitric oxide synthase. *Bioorg. Med. Chem.* 2012, 20, 2435-2443; Hevel, J. M. and Marletta, M. A. "Nitric-Oxide Synthase assays" in *Methods in Enzymology*, 1994, 233, 250-258.) The apparent $K_i$ values and isoform selectivities are summarized in Table 1, and values for compounds 1, 2, and 3 are included for comparative purposes; the $IC_{50}$ values for 4 are given in FIG. 1. (Likewise, various compounds of FIGS. 2-3 were similarly assayed, with data available, but not reported herein.)

TABLE 1

Inhibition of NOS enzymes by compounds 5-16.

| Compound | $K_i$ (μM)[a] nNOS | iNOS | eNOS | Selectivity n/i | n/e |
|---|---|---|---|---|---|
| 1 | 0.014 | 4.1 | 28 | 293 | 2000 |
| 2 | 0.007 | 5.8 | 19.2 | 807 | 2676 |
| 3 | 0.011 | 1.6 | 0.9 | 149 | 82 |
| 5 (Ex. 8) | 0.075 | 9.14 | 0.485 | 124 | 6.2 |
| 6 (Ex. 12) | 0.254 | 24.5 | 7.77 | 97 | 30 |
| 7 (Ex. 13) | 0.049 | 44.0 | 11.16 | 899 | 228 |
| 8 (Ex. 21) | 0.164 | 31.9 | 7.25 | 194 | 44 |
| 9 (Ex. 9) | 0.060 | 32.3 | 3.69 | 538 | 62 |
| 10 (Ex. 25) | >5.7 | NT | NT | ND | ND |
| 11 (Ex. 28) | >5.7 | NT | NT | ND | ND |
| 12 (Ex. 29) | >5.7 | NT | NT | ND | ND |
| 13 (Ex. 30) | 4.37 | NT | NT | ND | ND |
| 14 (Ex. 16) | 0.183 | 51.2 | 8.86 | 280 | 37 |
| 15 (Ex. 17) | 0.066 | 28.4 | 7.24 | 431 | 110 |
| 16 (Ex. 18) | 0.212 | 19.2 | 9.89 | 91 | 47 |

[a]The compounds were assayed for in vitro inhibition against three purified NOS isoforms: rat nNOS, bovine eNOS and murine iNOS, using known literature methods (see experimental section for details), and $K_i$ values, calculated directly from $IC_{50}$ values, are the average of at least two replicates; selectivity values are ratios of respective $K_i$ values. NT = not tested, ND = not determined.

The lead 7-substituted 2-aminoquinoline, compound 5, has potent nNOS inhibitory activity and high n/i selectivity, yet it is only weakly selective for nNOS over eNOS. It was hypothesized that this low selectivity arose from the lack of contact between the fluorophenyl tail of the inhibitor and a hydrophobic pocket consisting of Tyr706, Leu337, and Met336 (the last of which is present in nNOS and iNOS, but is a valine in eNOS). Contact with these residues is implicated for high potency and isoform selectivity, and in the case of 5, it was predicted that the short fluorophenethyl group would instead sit out in the substrate access channel, where it could fit just as easily into the larger, looser hydrophobic pocket of eNOS (Tyr477, Leu107, and Val106). Indeed, the crystal structures of 5 bound to both nNOS and eNOS (FIGS. 4A and 4B, respectively) indicate that the bound conformation of 5 is virtually identical in both isoforms, a result that easily explains the low selectivity. In both cases, without restriction to any one theory or mode of operation, the aminoquinoline moiety can act as an arginine mimic and interacts with the active site glutamate (Glu 592 in nNOS; Glu363 in eNOS). The secondary amine sits between the heme propionates and could form hydrogen bonds with both carboxylates, while the fluorophenethyl moiety, as predicted, does not quite reach the hydrophobic pocket except for slight contact between the fluorine atom and Leu337; this is similar to the crystal structure of 3. To establish hydrogen bonds between both the amine group and heme propionates and between the aminoquinoline and Glu592, the rigid quinoline plane must tilt significantly from the heme plane.

Because of the low n/e selectivity of 5, improved potency and n/e selectivity were sought by elongating the chain between the aminoquinoline and the non-coordinating aryl ring. To this end, extra methylene groups were inserted between the secondary amine and fluorophenyl group (9), or between the quinoline and the secondary amine (7, 8). It was reasoned that moving the amine farther from the quinoline could also have the advantage of relaxing the constraints on the quinoline ring orientation but still allow the amine to interact with the heme propionates, thus, in turn, anchoring the tail in a favorable orientation to make hydrophobic contacts. Following that same rationale, compound 6 was also prepared.

Without limitation, there are two factors that can affect the comparative inhibitor potency in this series of aminoquinoline compounds: the linker length and the position of the amine group. Contrary to the prediction regarding amine position, the structure of nNOS with 6 bound (FIG. 5A) reveals that placing two carbons between the quinoline and the amine actually diminishes the interaction with the heme propionates (more than 3.6 Å distance), leading to increased flexibility as evidenced by the disordered fluorophenethyl tail in the structure and decreased potency relative to 5. Superimposition of these two nNOS structures (5 and 6, FIG. 5B)

reveals that the loose interaction between the amine of 6 and the heme propionates (because of the more flexible chain) allows the quinoline to assume a more parallel orientation (relative to the heme) than observed in the structure of 5. However, as the 4-atom linker (of 5 and 6) is not long enough to bring the fluorophenyl ring in contact with the aforementioned hydrophobic pocket, the majority of the stabilization results from the hydrogen bonds from the aminoquinoline and the linker amine. Therefore, 5, with an extra hydrogen bond, is a stronger inhibitor than 6.

Figure 6A:
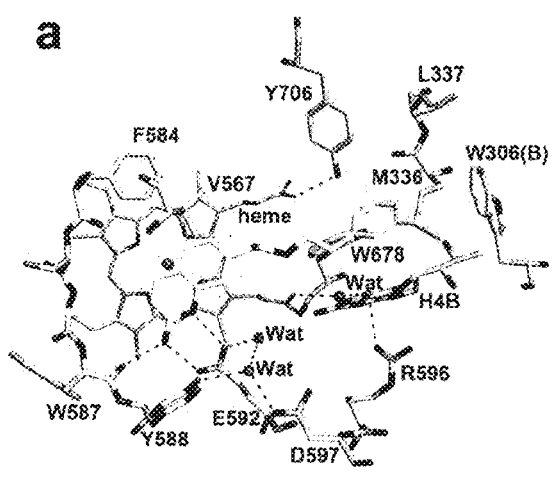
FIGS. 6A-B. Active site structure of 7 (A) or 9 (B) bound to nNOS. The omit Fo-Fc density map for the inhibitor is shown at 2.5 σ contour level. The fluorophenethyl tail of 7 shows weaker density indicative of disordering. Major hydrogen bonds are shown as dashed lines.

The influence of the linker amine is weakened in inhibitors with longer linker lengths. A general trend in linker length is evidenced by compounds with shorter linkers (5 and 6) having lower nNOS inhibitory activity than compounds with longer linkers (7 and 9, Table 1). The ideal chain length thus appears to be five atoms between the quinoline and fluorophenyl groups. nNOS inhibitory activity is similar between 7 and 9 (FIGS. 6A and 6B), with the nitrogen placement not drastically affecting potency, whereas compound 8 (FIG. 7A), which has six atoms between the fluorophenyl group and aminoquinoline, is less potent. The omit electron density map reveals that 7 (FIG. 6A), which does not have a strong secondary amine-heme propionate interaction, appears to be more flexible/disordered in the fluorophenyl tail region relative to the structure of 9, (which does show the amine-propionate interaction and an ordered fluorophenyl tail, like 5), yet their potencies are very similar, indicating that the nitrogen position may not be as crucial for these compounds with longer linkers. Indeed, the structure of 9 (FIG. 6B) shows numerous favorable hydrophobic contacts between the fluorophenyl group and the nonpolar residues at the far end of the substrate access channel (Tyr706, Leu337, Met336, and Trp306 of chain B). Although the crystal structure shows that the tail of 7 is more disordered than that of 9, these hydrophobic contacts exist with 7 as well. When the linker is long enough to allow contact between the fluorophenyl ring and the hydrophobic pocket, the combined stabilization from both the hydrophobic interactions and the aminoquinoline-Glu592 interaction may effectively outweigh any lack of interaction between the secondary amines and heme propionates.

Figure 6B:
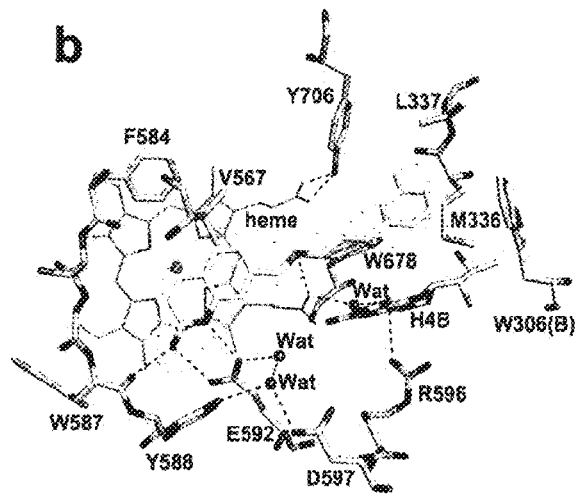
Figure 7A:
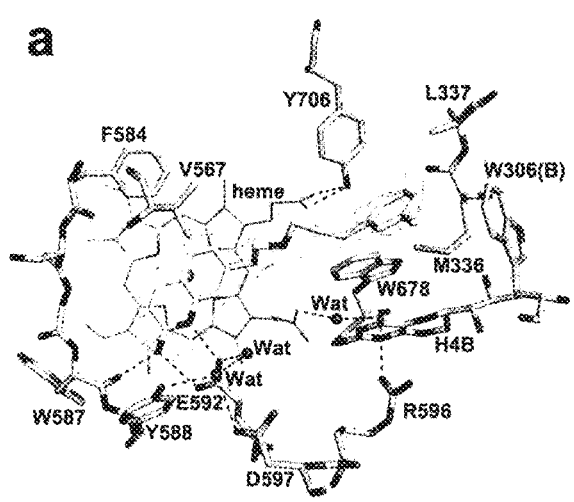
FIGS. 7A-B. Active site structure of 8 (A) or 15 (B) bound to nNOS. The omit Fo-Fc density map for inhibitor is shown at 2.5 σ contour level. The chlorophenethyl tail of 15 is partially disordered with weaker density. Major hydrogen bonds are shown as dashed lines.
Figure 7B:
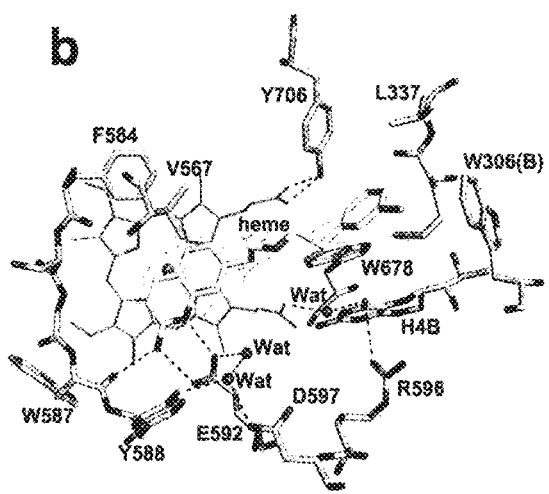

Chain lengths that are longer than the ideal (e.g., compound 8) result in a drop in potency when compared with 7 or 9. The crystal structure (FIG. 7A) shows that the fluorophenyl ring of 8 makes the same hydrophobic contacts as 7 and 9. Nonetheless, to make these contacts, the flexible chain has to assume a "kinked" conformation, in contrast to the fully extended linker conformation seen in 9 (FIG. 6B). The kinked conformation of 8 may result in unfavorable torsional strain in the linker region upon binding.

Compounds 7, 9, and 15 have $K_i$ values of 44 µM, 32.3 µM, and 51.2 µM, respectively, and 7 has nearly 900-fold selectivity for nNOS over iNOS, a value which is significantly higher than those of 1-4, and is among the highest selectivity reported for nNOS over iNOS for non-peptidic inhibitors. Any contact with the substrate-channel hydrophobic pocket (vide supra) could improve n/i selectivity. Murine iNOS contains a polar asparagine residue (Asn115) in this pocket (at the position of Leu337 of nNOS) that would strongly disfavor binding by a hydrophobic group. Nonetheless, even the short-chain inhibitors (5 and 6) still possess good n/i selectivity, despite not reaching this distal pocket, indicating that interactions with residues at this end of the binding site are not the full determinant of this poor iNOS inhibition.

It is reported that the heme-binding sites themselves differ between iNOS and nNOS isoforms, with the former possessing a smaller active site that may not tolerate the bulky and rigid aminoquinoline as well. Interestingly, the selectivity patterns (higher n/i selectivity) contrast with many aminopyridine-based inhibitors, which have higher n/e selectivity. In some cases (such as the R,R-enantiomer of 1), this high n/e selectivity can be explained by water-mediated contacts made between the center pyrrolidine ring and Asp597, a residue that exists in both nNOS and iNOS but is Asn369 in eNOS. This aspartate residue can provide considerable electrostatic or hydrogen-bonding stabilization in nNOS versus eNOS; this stabilization also manifests itself in the high n/e selectivity of dipeptide-based inhibitors but no contacts with Asp597 are observed in the aminoquinoline crystal structures.

Figure 8:
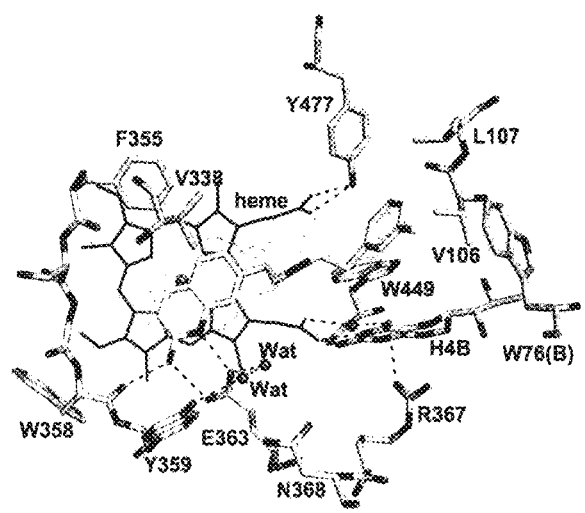
FIG. 8. Active site structure of 7 bound to eNOS. The omit Fo-Fc density map for the inhibitor is shown at 2.5 σ contour level. The fluorophenethyl tail of 7 shows weaker density indicative of partial disordering. Major hydrogen bonds are shown as dashed lines.

In other cases, high n/e selectivity is rationalized by the tighter pi-stacking with Tyr706 of nNOS than with the analogous Tyr477 of eNOS, leading to greater nonbonded contacts and better desolvation. While no clear pi-stacking interactions are visible in the nNOS crystal structures of 6, 7, 8, or 9, hydrophobic contacts and desolvation may still play a substantial role in n/e selectivity for aminoquinolines. The binding mode of the aminoquinoline portion is identical in the structure of 7 bound to nNOS (FIG. 6A) or eNOS (FIG. 8) and does not contribute to isoform selectivity. However, the length of the linker in 7 enables the fluorophenyl ring to make good hydrophobic contacts with the residues Met336, Leu337, Tyr706, and Trp306 from the other subunit. The bulky and flexible Met336 side chain makes extensive contacts with the fluorophenyl group of 7, whereas the analogous residue, Val106 in eNOS, with a smaller surface area, cannot make these contacts. Additionally, the side chain of Tyr706 in nNOS rotates by about 60° in order to make better contacts with the tail of 7, while in the eNOS structure (FIG. 8) Tyr477 remains in its original side chain orientation. Overall, these differences are fairly subtle but still contribute to the slightly tighter binding of 7 to nNOS over eNOS. Small changes in these hydrophobic contacts could also explain why 7 is more selective than 9.

Figure 5A:
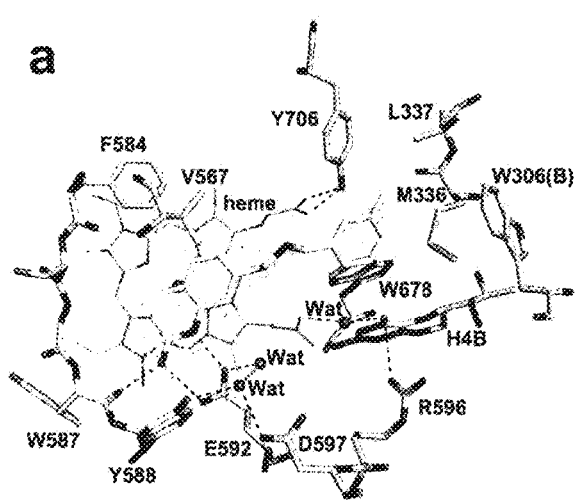
FIGS. 5A-B. (A) Active site structure of 6 bound to nNOS. The omit Fo-Fc density map for the inhibitor is shown at 2.5 σ contour level. The fluorophenethyl tail is partially disordered with weaker density. (B) Overlay of 5 (yellow) and 6 (cyan) showing the different tilt angles of the aminoquinoline ring relative to the heme plane in cases where a hydrogen-bond (dashed line) from the heme propionate to the linker amine is present (compound 5) or absent (compound 6).
Figure 5B:
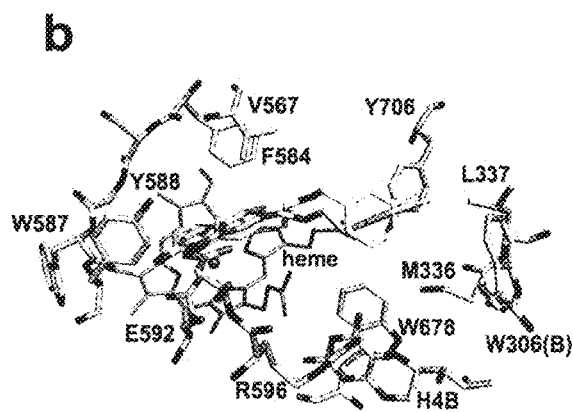

While 7-substituted aminoquinolines (5-9, 14-16) are all highly potent against nNOS, the analogous 6-substituted aminoquinolines 10-13 have low potency, regardless of chain length or nitrogen position. This disparity is also explained by the crystal structures of the bound 2-aminoquinolines. In the heme-binding pocket, the aminoquinoline system does not stack parallel to the heme, but rather tilts down slightly toward the "back wall" of this pocket (FIGS. 5A and 5B). In cases where a H-bond is formed between the secondary amine and heme propionates, the angle between the planes of the aminoquinoline and heme can be as large as 45°, held in this conformation by the H-bond. Even when no hydrogen bond is present, the aminoquinoline still tilts to avoid unfavorable contact with Val567 and Phe584, bulky residues that project downward from the roof of this pocket. A large or flexible substituent located at position 6, in any case, would clash directly with these bulky residues or the heme propionates, or force the rigid aminoquinoline system into a position where it can no longer be accommodated in the heme-binding pocket. This also explains why 4, a flexible ligand, has very potent nNOS inhibitory activity, despite sharing a similar overall structure with the rigid 6-substituted aminoquinoline 12. It also was reported in the literature that rigid fused 2-aminodihydroquinoline-based nNOS inhibitors show a similar SAR regarding substituent placement; large amine-containing tails can be easily placed in the region analogous to the 7-position, whereas the area occupied by the "6-position" can only fit small substituents, such as fluorine.

Figure 4A:
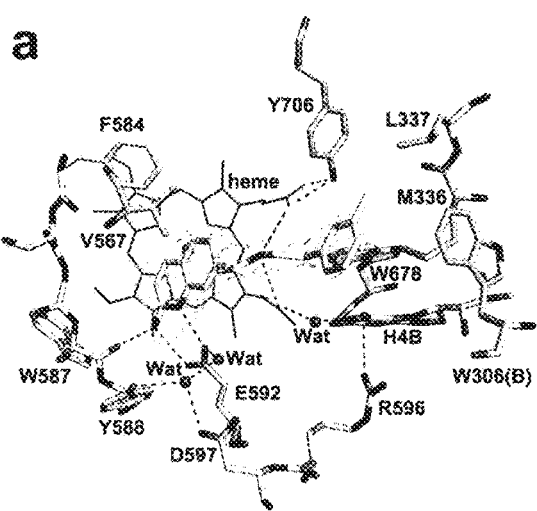
FIGS. 4A-B. Active site structures of lead 5 (FIG. 1) bound to rat nNOS (A) and bovine eNOS (B). The omit Fo-Fc density map for the inhibitor is shown at 2.5 σ contour level. Major hydrogen bonds are shown as dashed lines.
Figure 4B:
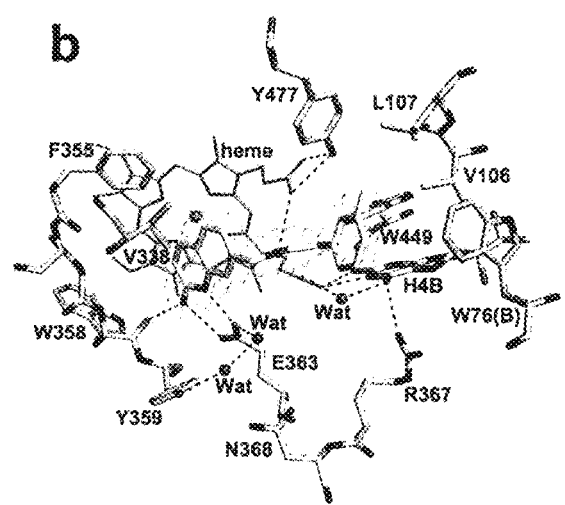

Interestingly, the replacement of the fluorine in the 3-fluorophenyl group of 7 with a bulkier chlorine (compound 15) does not significantly decrease nNOS inhibitory potency of 15 and is only modestly detrimental to isoform selectivity, which remains 431-fold and 110-fold for iNOS and eNOS, respectively. As shown in FIG. 5b, 15 binds to nNOS in a manner very similar to 7 (FIG. 4a). Without a strong interaction between the amine and the heme propionates, the chlorophenethyl tail is partially disordered, but can still be located based on the partial density contoured at 0.5 σ. In this model, the chlorine atom is not pointing directly into the hydrophobic pocket, so the switch between chlorine and fluorine should not significantly alter contacts with the enzyme. Placement of the fluorine (or chlorine) at the 4-position, however, is a disfavored modification (compare 7 to 14 or 15 to 16). This drop in potency could arise from unfavorable steric clashes between the 4-position substituent (which would face directly toward the back of the hydrophobic pocket) and any hydrophobic pocket residue, especially Met336 and Leu337.

Encouraged by the high potency and selectivity of 7 and 15, these compounds (and lead 5) were assayed against purified human nNOS (Table 2). The human isoform has an active site that is nearly identical to that in the rat enzyme, with the exception of the hydrophobic pocket, where Leu337 is replaced by a histidine (His341). This pocket is smaller and more polar, and may prefer to bind inhibitors with less bulky and more hydrophilic tails. Previously, aminopyridine-based inhibitors showed lower potency against the human enzyme when compared to the rat enzyme, and the same trend is observed for the aminoquinolines, although 5, 7, and 15 still display good nNOS inhibition. Because of the very similar selectivities ($K_i$-human/$K_i$-rat) among these three compounds, it can be concluded that the modifications that are well tolerated by the rat isoform (chain elongation and replacement of fluorine with chlorine) are likewise tolerated similarly by human nNOS, including the introduction of the bulkier chlorine.

TABLE 2

Inhibition of rat and human nNOS by compounds 5, 7, and 15.

| | $K_i$ (μM) | | |
|---|---|---|---|
| Compound | Rat nNOS | Human nNOS | Selectivity (Rat/Human) |
| 5 | 0.074 | 0.493 | 6.7 |
| 7 | 0.049 | 0.318 | 6.5 |
| 15 | 0.066 | 0.440 | 6.7 |

[a]See Table 1 and experimental section for details of assay. $K_i$ values, calculated directly from $IC_{50}$ values, are the average of at least two replicates; selectivity values are ratios of respective $K_i$ values.

Finally, compounds 7 and 15 were assayed in a Caco-2 monolayer permeability assay (Table 3). This assay is an approximation of both a compound's ability to penetrate the epithelium of the GI tract as well as the blood-brain barrier; ideally an orally bioavailable nNOS inhibitor should show high permeability in this assay. An efflux ratio (ratio of membrane permeability (A→B) to efflux (B→A))<3 is considered favorable. Pleasingly, both 7 and 15 display good membrane permeability in the apical to basolateral direction and high compound recovery values. Compound 15 even shows improved membrane permeation relative to compound 4, and both 7 and 15 display relatively low efflux ratios, diminishing the possibility that P-gp or other active transport mechanisms are significantly acting on these compounds (especially on 15). Interestingly, compound 15 is more membrane-permeable than 7 despite their nearly identical structures; this could be the result of the higher cLogP of 15 (3.8) relative to 7 (3.2) or to variability in the assay.

TABLE 3

Caco-2 permeability summary for select compounds.

| | Apparent Permeability ($P_{app}$, $10^{-6}$ cm s$^{-1}$)[b] | | | Recovery | |
|---|---|---|---|---|---|
| Compound | Mean A-->B | Mean B-->A | Efflux ratio | A-->B | B-->A |
| 4 | 27.3 | 34.2 | 1.3 | 113% | 78% |
| 7 | 16.9 | 41.9 | 2.5 | 63% | 103% |
| 15 | 30.3 | 24.5 | 0.8 | 98% | 67% |
| Warfarin[c] | 46.8 | 15.7 | 0.3 | — | — |
| Ranitidine[d] | 0.5 | 3.8 | 7.2 | — | — |
| Talinolol[e] | 0.1 | 10.2 | 77.7 | — | — |

[a]All assays were performed over 2 h at a concentration of 10 μM. See experimental section for details.
[b]Apparent permeability value.
[c]High permeability control;
[d]low permeability control;
[e]high efflux control.

The present invention can also, as would be understood by those skilled in the art, be extended to or include methods using or in conjunction with a pharmaceutical composition comprising an inhibitor compound of the sort described herein in a physiologically or otherwise suitable formulation. In some embodiments, the present invention includes one or more such inhibitors, as outlined above or discussed more fully below, formulated into compositions together with one or more physiologically tolerable or acceptable diluents, carriers, adjuvants or vehicles that are collectively referred to herein as carriers. Compositions suitable for such contact or administration can comprise physiologically acceptable sterile aqueous or non-aqueous solutions, dispersions, suspensions or emulsions. The resulting compositions can be, in conjunction with the various methods described herein, for administration or contact with a human/animal enzyme expressed or otherwise present therein. Whether or not in conjunction with a pharmaceutical composition, "contacting" means that a nitric oxide synthase and one or more inhibitor compounds are brought together for purpose of binding and/or complexing such an inhibitor compound to the enzyme. Amounts of a compound effective to affect or otherwise inhibit a nitric oxide synthase may be determined empirically, and making such determinations is within the skill in the art. Inhibition, affecting or otherwise modulating nitric oxide synthase activity includes both reduction and/or mitigation, as well as elimination of NOS activity and/or nitric oxide production.

It is understood by those skilled in the art that dosage amount will vary with the activity of a particular inhibitor compound, disease state, route of administration, duration of treatment and like factors well-known in the medical and pharmaceutical arts. In general, a suitable dose will be an amount which is the lowest dose effective to produce a therapeutic or prophylactic effect. If desired, an effective dose of such a compound, pharmaceutically acceptable salt thereof or related composition may be administered in two or more sub-doses, administered separately over an appropriate period of time.

Methods of preparing pharmaceutical formulations or compositions include the step of bringing an inhibitor compound into association with a carrier and, optionally, one or more additional adjuvants or ingredients. For example, standard pharmaceutical formulation techniques can be employed, such as those described in Remington's Pharmaceutical Sciences, Mac Publishing Company, Easton, Pa.

Regardless of composition or formulation, those skilled in the art will recognize various avenues for medicament administration, together with corresponding factors and parameters to be considered in rendering such a medicament suitable for administration. Accordingly, with respect to one or more non-limiting embodiments, the present invention provides for use of one or more inhibitor compounds for the manufacture of a medicament for therapeutic use in the treatment or prevention of disease states indicated by high nitric oxide production and/or associated neuronal damage and degeneration.

As discussed above, the present invention provides a series of simplified 2-aminoquinoline compounds based on the rationale that they might bind to and inhibit nNOS in a manner similar to aminopyridines, while being less polar, less basic, more lipophilic, and, therefore, more bioavailable. Compounds were assayed with purified NOS enzymes, and it was revealed that, in particular, 7-substituted 2-aminoquinolines are highly potent inhibitors of nNOS, and that subtle modifications (such as increasing the chain length between the aminoquinoline and a non-coordinating aryl ring) can enhance potency and greatly improve isoform selectivity to >100-fold over both iNOS and eNOS. Crystal structures indicate that these compounds act as competitive arginine mimics, where the aminoquinoline moiety makes hydrogen bonds with the active-site glutamate residue, and the non-coordinating aryl rings are stabilized in a hydrophobic pocket on the far end of the substrate access channel. Enhanced hydrophobic contacts with 7 in this pocket in nNOS, relative to that of eNOS, may also, in part, dictate the high isoform selectivity. Most promisingly, two of these highly effective compounds, 7 and 15, show good permeability in a Caco-2 assay. These results indicate that these compounds have high potential for oral bioavailability and brain penetration, and that the 7-substituted 2-aminoquinoline cores offer very promising leads for further nNOS inhibitor development.

EXAMPLES OF THE INVENTION

The following non-limiting examples and data illustrate various aspects and features relating to the compounds and/or methods of the present invention, including the preparation of various nitric oxide synthase inhibitor compounds, as are available through the synthetic methodologies described herein. In comparison with the prior art, the present compounds and/or methods provide results and data which are surprising, unexpected and contrary thereto. While the utility of this invention is illustrated through the use of several compounds and moieties/groups which can be used therewith, it will be understood by those skilled in the art that comparable results are obtainable with various other compounds, moieties and/or groups, as are commensurate with the scope of this invention.

General Procedures. Anhydrous solvents (THF, $CH_2Cl_2$, and DMF) were distilled prior to use. The remaining solvents, reactants, and reagents were purchased from commercial vendors and were used without further purification, with the exception of acetamide, which was heated to 80° C. and dried under vacuum before use. Melting points were determined in capillary tubes using a Buchi Melting Point B-540 apparatus, and are uncorrected. $^1H$ NMR spectra were recorded at 500 MHz, using a Bruker Avance III 500 (direct cryoprobe), and $^{13}C$ NMR spectra were obtained at 126 MHz using the same instrument. Low-resolution ESIMS was performed using a Thermo Finnigan LCQ system. High-resolution mass spectral data were obtained at the Integrated Molecular Structure Education and Research Facility (Northwestern University) on an Agilent 6210A TOF mass spectrometer in positive ion mode using electrospray ionization, with an Agilent G1312A HPLC pump and an Agilent G1367B autoinjector. Data were processed using MassHunter software version B.02.00. Flash column chromatography was performed using an Agilent 971-FP automated flash purification system, using a Varian column station with SiliCycle cartridges (8-80 g), or manually in glass columns using SiliCycle SiliaFlash P60 40-63 μM silica gel. Analytical HPLC was performed either using a Beckman System Gold 125 solvent module and 166 Detector, or an Agilent Infinity 1260 system and an injection volume of 10 μL. A Phenomenex Gemini C18 5μ 110 Å reverse-phase column, Gemini NX 5μ 100 Å column (both with dimensions of 250 mm×4.6 mm), or Phenomenex Synergi 5μ polar RP column (4.6×50 mm) was used for all HPLC experiments. The purity of all target compounds was found to be ≥95% by HPLC, using either isocratic elution at 70% MeOH in $H_2O$ (with 0.1% TFA), or a gradient of 65-95% MeOH in $H_2O$ (with 0.1% TFA), at 0.8 mL/min. When the polar RP column was used, elution was isocratic at either 50% acetonitrile in $H_2O$ or 35% acetonitrile in $H_2O$, at 1.5 mL/min. Preparative HPLC was performed at the Northwestern University Center for Molecular Innovation and Drug Discovery ChemCore lab, using an Agilent 1200 Series HPLC and Agilent 6120 Quadrupole Mass Spectrometer (API-MS mode) and a Phenomenex Gemini-NX 5 μm C18 column (150×21.2 mm). Analytical thin-layer chromatography was performed on Silicycle extra hard 250 μM TLC plates. Compounds were visualized with short-wavelength UV light, ninhydrin, and $KMnO_4$ stain, where relevant. Compounds 17, 35, 36, and 42 were prepared by literature procedures, and their spectral data are consistent with those data reported for the same.

Example 1

7-Methylquinolin-2(1H)-one (18a) and 5-Methylquinolin-2(1H)-one (18b). Compound 17 (4.26 g, 18.0 mmol) was diluted in chlorobenzene (45 mL) and anhydrous $AlCl_3$ (12.0 g, 5.00 mmol) was added. The mixture was heated to 90° C. for 2 h, upon which the solution became black. The solution was cooled and poured into ice-$H_2O$ (300 mL), which was extracted with EtOAc (2×300 mL). The organic phase was washed with $H_2O$ (200 mL), and the aqueous layer was extracted with EtOAc (100 mL). The combined organic layers were washed with sat. aq. NaCl (200 mL) and dried over anhydrous sodium sulfate. The orange solution was filtered through Celite and concentrated to afford the mixture of products as a beige solid (2.53 g, 88%) after washing with hexanes and drying. $^1H$ NMR spectra indicated that 18a and 18b were present as a 70:30 mixture (consistent with prior reports), which was used without any further purification.

Example 2

2-Chloro-7-methylquinoline (19a). A mixture of 18a and 18b (2.53 g, 15.9 mmol) was diluted in $POCl_3$ (~35 mL), and the mixture was heated at reflux for 70 min, before the clear orange solution was cooled to room temperature and poured into ice-$H_2O$ (300 mL) in a large beaker. The beaker was immersed in ice and cooled to 0° C. with stirring, and solid NaOH was added until the pH of the mixture was approximately 7. The resultant cloudy suspension was extracted with EtOAc (300 mL) and the organic layers were washed with $H_2O$ (100 mL) and sat. aq. NaCl (100 mL). The organic layer was dried over anhydrous sodium sulfate, concentrated, and the residue was purified by flash column chromatography ($SiO_2$), eluting with a gradient of hexanes to 12% ethyl acetate in hexanes to afford orange crystals. Fractional crystallization from hot isopropanol yielded pure 19a (0.850 g, 30%) as light orange iridescent crystals; the analytical data for this compound is identical to prior literature reports. H-NMR (500 MHz; CDCl$_3$): δ 8.05 (d, J=8.5 Hz, 1 H), 8.00 (m, 1 H), 7.71 (d, J=8.3 Hz, 1 H), 7.39 (dd, J=8.3, 1.5 Hz, 1 H), 7.32 (d, J=8.5 Hz, 1 H), 2.56 (s, 3 H).

Example 3

2-(Acetamido)-7-methylquinoline (20). Chloride 19a (0.300 g, 1.69 mmol) was diluted with molten anhydrous acetamide (8 g, 135 mmol) and K$_2$CO$_3$ (1.17 g, 8.45 mmol) was added. The mixture was heated in a sand bath, at reflux (~230° C.) for 17 h. The mixture was cooled, poured into H$_2$O (120 mL) and extracted with EtOAc (4×30 mL). The organic layers were washed with H$_2$O (3×100 mL) and sat. aq. NaCl (50 mL), dried over anhydrous sodium sulfate, and concentrated. Purification of the residue by flash column chromatography (SiO$_2$, 15% EtOAc in CH$_2$Cl$_2$) afforded the desired compound as a white solid (0.265 g, 78%). $^1$H-NMR chemical shifts for this compound are consistent with those reported in the literature for the 7-isomer. H-NMR (500 MHz; CDCl$_3$): δ 9.89-9.88 (br s, 1 H), 8.40 (d, J=8.9 Hz, 1 H), 8.15 (d, J=9.0 Hz, 1 H), 7.67 (d, J=8.3 Hz, 1 H), 7.58 (d, J=0.6 Hz, 1 H), 7.29 (dd, J=8.3, 1.4 Hz, 1 H), 2.54 (s, 3 H), 2.27 (s, 3 H).

Example 4

2-(Acetamido)-7-(bromomethyl)quinoline (21). Compound 20 (0.265 g, 1.32 mmol) was diluted in anhydrous benzene (10 mL). N-Bromosuccinimide (0.247 g, 1.39 mmol) and a catalytic amount (0.020 g) of benzoyl peroxide were added, and the mixture was heated to reflux under argon until an orange tint was no longer visible in the solution refluxing in the condenser (typically 4 h). The mixture was cooled, concentrated, and purified by flash column chromatography (SiO$_2$), eluting with a gradient of 7% to 14% EtOAc in CH$_2$Cl$_2$, to yield the product (0.236 g, 64%) as a flocculent yellow solid. $^1$H NMR chemical shifts for this compound are consistent with those reported in the literature for the 7-isomer. $^1$H-NMR (500 MHz; CDCl$_3$): δ 8.43-8.41 (m, 2 H), 8.16 (d, J=8.9 Hz, 1 H), 7.79-7.77 (m, 2 H), 7.49 (dd, J=8.4, 1.7 Hz, 1 H), 4.65 (s, 2 H), 2.27 (s, 3 H).

Example 5

3-Fluorophenethyl Cyanide (24). 3-Fluorophenethyl bromide (23, 1.00 g, 12.3 mmol) was diluted in dry DMF (25 mL). Sodium cyanide (1.06 g, 61.6 mmol) was added in one portion, and the mixture was heated to 60° C. under argon for 16 h. The mixture was cooled and concentrated, and the residue was partitioned between EtOAc and H$_2$O (50 mL each). The layers were separated, and the aqueous phase was extracted with EtOAc (2×20 mL). The organic layers were washed with H$_2$O and sat. aq. NaCl (50 mL each), dried over anhydrous sodium sulfate, and concentrated. The resulting oil was purified by flash column chromatography (SiO$_2$), eluting with a gradient of 5% EtOAc in hexanes to 30% EtOAc in hexanes to yield the desired product as a colorless oil (0.638 g, 87%). $^1$H-NMR (500 MHz; CDCl$_3$): δ 7.31 (td, J=7.9, 6.0 Hz, 1 H), 7.03-6.93 (m, 3 H), 2.96 (t, J=7.4 Hz, 2 H), 2.63 (t, J=7.4 Hz, 2 H).

Example 6

3-(3-Fluorophenyl)-propan-1-amine (25). Compound 24 (0.180 g, 1.21 mmol) was diluted in EtOH (3 mL) and methanolic ammonia (7 M, 6 mL) and Raney nickel (~1 g) were added. The mixture was degassed and hydrogenated with a H$_2$-filled balloon for 30 minutes. The mixture was filtered through a Pall 0.2 μm syringe filter and concentrated to yield a sticky green syrup (0.083 g, 45%). The presence of amine was confirmed by $^1$H NMR spectrometry, TLC, and ninhydrin staining, and this material was used crude without any further purification.

Example 7

2-Acetamido-7-[(3-fluorophenethylamino)methyl]quinoline (26). Anhydrous Cs$_2$CO$_3$ (0.295 g, 0.906 mmol) was diluted in anhydrous DMF (10 mL). 3-Fluorophenethylamine (22, 0.126 g, 0.906 mmol) was added, and the mixture was stirred at room temperature for 30 min before a solution of 21 (0.220 g, 0.788 mmol) in DMF (4 mL) was added slowly over 5 min. The cloudy yellow mixture was stirred at room temperature for 16 h and concentrated. The residue was diluted with EtOAc (50 mL) and washed with H$_2$O (2×50 mL) and sat. aq. NaCl (50 mL). The organic phase was dried over anhydrous sodium sulfate, concentrated, and purified by flash column chromatography (SiO$_2$) eluting with 10% MeOH in EtOAc to yield the product as a clear yellow oil (0.187 g, 70%). $^1$H-NMR (500 MHz; CDCl$_3$): δ 8.95 (s, 1 H), 8.40 (br d, J=8.2 Hz, 1 H), 8.15 (d, J=8.9 Hz, 1 H), 7.74 (d, J=8.3 Hz, 1 H), 7.72 (s, 1 H), 7.41 (dd, J=8.3, 1.5 Hz, 1 H), 7.26-7.22 (m, 1 H), 6.98 (d, J=7.7 Hz, 1 H), 6.93-6.88 (m, 2 H), 4.00 (s, 2 H), 2.95 (t, J=7.0 Hz, 2 H), 2.85 (t, J=7.0 Hz, 2 H), 2.23 (s, 3 H); $^{13}$C NMR (126 MHz; CDCl$_3$): δ 169.3 (1 C), (163.9+162.0, 1 C), 151.3 (1 C), 146.5 (1 C), (142.47+142.41, 1 C), 142.37 (1 C), 138.5 (1C), (129.95+129.88, 1 C), 127.8 (1 C), 125.76 (1 C), 125.71 (1 C), 125.4 (1 C), (124.42+124.40, 1 C), (115.63+115.46, 1 C), 114.0 (1 C), (113.23+113.06, 1 C), 53.7 (1 C), 50.1 (1 C), 36.1 (1 C), 24.9 (1 C); ESIMS m/z (rel. intensity) 338 (MH$^+$, 80).

Example 8

7-[(3-Fluorophenethylamino)methyl]quinolin-2-amine Dihydrochloride (5). Compound 26 (0.187 g, 0.554 mmol) was diluted in MeOH (8 mL) and K$_2$CO$_3$ (0.077 g, 0.554 mmol) was added. The mixture was heated at 50° C. for 2 h, and then at reflux for an additional 1 h. The mixture was cooled and concentrated, and the residue was diluted in EtOAc (50 mL), washed with H$_2$O (2×50 mL), and dried over anhydrous sodium sulfate. The solution was concentrated and the residue was diluted in methanolic HCl (~1.4 M, 12 mL), and the mixture was heated for 3 h at 50° C., upon which a white crystalline precipitate formed. The mixture was cooled and filtered, and additional product was obtained upon concentration of the filtrate and recrystallization of the residue from MeOH. A total of 0.140 g of product (69%) was obtained: mp 283-285° C. (dec.); $^1$H-NMR (500 MHz; DMSO-d$_6$): δ 14.47 (s, 1H), 9.65 (br s, 2 H), 9.31 (br m, 1 H), 8.39 (d, J=9.3 Hz, 1 H), 8.30 (br s, 1 H), 7.99 (d, J=8.2 Hz, 1 H), 7.87 (s, 1 H), 7.68 (d, J=8.5 Hz, 1 H), 7.40 (td, J=7.8, 6.4 Hz, 1 H), 7.16-7.09 (m, 4 H), 4.36-4.35 (m, 2 H), 3.23-3.22 (m, 2 H), 3.06 (t, J=8.1 Hz, 2 H); $^{13}$C-NMR (126 MHz; DMSO-d$_6$): δ (163.2+161.3, 1 C), 154.7 (1 C), 142.6 (1 C), (140.09+140.03, 1 C), 136.5 (1 C), 135.5 (1 C), (130.60+130.53, 1 C), 129.1 (1 C), 126.5 (1 C), (124.82+124.81, 1 C), 120.9 (1 C), 118.8 (1 C), (115.53+115.36, 1 C), 114.5 (1 C), (113.70+113.54, 1 C), 49.5 (1 C), 47.3 (1 C), 31.0 (1 C); ESIMS m/z (rel. intensity) 296 (MH$^+$, 100); HRMS calcd for C$_{18}$H$_{18}$FN$_3$: 295.1485. found: 295.1487.

Example 9

7-{2-[3-(3-Fluorophenyl(propylamino)methyl]}quinolin-2-amine Dihydrochloride (9). Anhydrous $Cs_2CO_3$ (0.105 g, 0.322 mmol) was diluted with anhydrous DMF (3 mL), 25 (0.050 g, 0.322 mmol) was added as a solution in DMF (~2 mL), and the mixture was stirred for 30 min at room temperature. Compound 21 (0.075 g, 0.269 mmol) was then added as a solution in DMF (1.3 mL) over several minutes. The mixture was stirred at room temperature for 16 h and then concentrated. The residue was partitioned between EtOAc and $H_2O$ (10 mL each), the layers were separated, and the aqueous layer was saturated with NaCl and extracted with EtOAc (2×5 mL). The combined organic layers were washed with sat. aq. NaCl (10 mL), dried over anhydrous sodium sulfate, and concentrated. The residue was purified by flash column chromatography ($SiO_2$), eluting with a gradient of EtOAc to 15% MeOH in EtOAc to yield 27 as a yellow syrup (0.039 g, 41%), which was used without further characterization. This compound was diluted with anhydrous MeOH (6 mL), and anhydrous $K_2CO_3$ (0.031 g, 0.022 mmol) was added. The mixture was heated at reflux for 2 h 15 min, cooled, and concentrated. The residue was diluted with EtOAc (10 mL), and 3 mL each of $H_2O$ and sat. aq. NaCl were added. The layers were separated, the aqueous layer was extracted with EtOAc (3×4 mL), and the combined organic layers were washed with sat. aq. NaCl (4 mL), dried over anhydrous sodium sulfate, and concentrated. The residue was diluted with $CH_2Cl_2$ (5 mL), filtered to remove particulate matter, and re-concentrated. Methanolic HCl (~1.4 M, 3 mL) was added, the mixture was stirred for 5 min, and ether (30 mL) was added slowly until a white precipitate formed. This solid was collected and dried to afford the title compound as a white microcrystalline solid (0.029 g, 28% based on 21) after drying in vacuo: mp 250-252° C. (dec). $^1H$-NMR (500 MHz; DMSO-$d_6$): δ 14.44 (s, 1 H), 9.50 (s, 2 H), 9.30 (br s, 1 H), 8.39 (d, J=9.2 Hz, 1 H), 8.30 (br s, 1 H), 7.98 (d, J=8.2 Hz, 1 H), 7.86 (s, 1 H), 7.66 (d, J=8.3 Hz, 1 H), 7.35 (td, J=8.0, 6.4 Hz, 1 H), 7.15 (d, J=9.3 Hz, 1 H), 7.10-7.02 (m, 3 H), 4.32 (t, J=5.5 Hz, 2H), 2.95-2.90 (m, 2 H), 2.70 (t, J=7.6 Hz, 2 H), 2.00 (quintet, J=7.7 Hz, 2 H); $^{13}C$-NMR (126 MHz; DMSO-$d_6$): δ (163.2+161.3, 1 C), 154.6 (1 C), (143.67+143.61, 1 C), 142.6 (1 C), 136.6 (1 C), (130.32+130.25, 1 C), 129.0 (1 C), 126.4 (1 C), (124.47+124.45, 1 C), 120.9 (1 C), 118.7 (1 C), (115.08+114.91, 1 C), 114.5 (1 C), (112.95+112.78, 1 C), 49.3 (1 C), 46.0 (1 C), 31.5 (1 C), 26.7 (1 C), one of the aminoquinoline carbons is not visible due to baseline broadening; ESIMS m/z (rel. intensity) 310 ($MH^+$, 100); HRMS calcd for $C_{19}H_{20}FN_3$: 309.1641. found: 309.1645.

Example 10

2-(Acetamido)-7-(cyanomethyl)quinoline (28). Compound 21 (0.216 g, 0.773 mmol) was diluted with anhydrous DMF (10 mL), and NaCN (0.190 g, 3.87 mmol) was added. The orange mixture was stirred at room temperature for 17 h. The mixture was concentrated and partitioned between EtOAc and $H_2O$ (50 mL each), and the layers were separated. The aqueous phase was extracted with EtOAc (2×50 mL), the combined organic layers were washed with $H_2O$ (2×80 mL) and sat aq. NaCl (50 mL) and dried over anhydrous sodium sulfate and concentrated. The residue was purified by flash column chromatography ($SiO_2$), eluting with a gradient of 15% EtOAc in $CH_2Cl_2$ to 25% EtOAc in $CH_2Cl_2$ to yield the title compound as a white solid (0.109 g, 63%): mp 180-182° C. $^1H$-NMR (500 MHz; $CDCl_3$): δ 8.44 (dd, J=8.3, 0.4 Hz, 1 H), 8.27-8.22 (m, 1 H), 8.18 (d, J=9.0 Hz, 1 H), 7.81 (d, J=8.4 Hz, 1 H), 7.79 (s, 1 H), 7.40 (dd, J=8.3, 1.7 Hz, 1 H), 3.94 (s, 2 H), 2.28 (s, 3 H); $^{13}C$-NMR (126 MHz; $CDCl_3$): δ 169.2 (1 C), 151.5 (1 C), 138.8 (1 C), 132.1 (1 C), 128.7 (1 C), 126.2 (1 C), 125.6 (1 C), 124.9 (1 C), 117.3 (1 C), 114.7 (1 C), 25.1 (1 C), 24.0 (1 C); ESIMS m/z (rel. intensity) 473 ($2M+Na^+$, 100).

Example 11

2-(Acetamido)-7-[2-aminoethyl)]quinoline (29). Compound 28 (0.060 g, 0.266 mmol) was diluted in absolute EtOH (7 mL), and methanolic ammonia (7 N, 7 mL) was added. Raney nickel (~1.5 g, washed with $H_2O$ and MeOH) was added, and the mixture was degassed and hydrogenated with a $H_2$-filled balloon at room temperature for 30 min while stirring rapidly. The clear solution was decanted from the nickel and was filtered through a Pall 0.2 µm syringe filter to remove fine particulate matter. The solution was concentrated and dried in vacuo to yield an off-white semisolid (0.062 g, 100%). Conversion to this amine was confirmed by TLC and ninhydrin staining and was used crude without any further characterization or purification.

Example 12

7-[2-(3-Fluorobenzylamino)ethyl]quinolin-2-amine Dihydrochloride (6). To a solution of 29 (0.062 g, 0.266 mmol) in 5:1 $CHCl_3$/MeOH (6 mL) was added aldehyde 30 (0.033 g, 0.319 mmol) and anhydrous sodium sulfate (approximately 0.5 g). The mixture was stirred rapidly for 90 min, and additional $Na_2SO_4$ (~0.3 g) and a catalytic amount of glacial AcOH (approximately 10 µL) was added. After a total of 3 h, extra $Na_2SO_4$ (~0.3 g) was added. After 4 h, TLC indicated consumption of amine 29, and the mixture was filtered to remove the $Na_2SO_4$ and the filter cake was washed with 10 mL of $CHCl_3$. The mixture was concentrated and the oily residue was diluted in MeOH (5 mL), then $NaBH_4$ (0.015 g, 0.4 mmol) was added. After being stirred for 20 min at room temperature, the solution was concentrated, and the residue was partitioned between EtOAc and $H_2O$ (20 mL each). The layers were separated, and the aqueous layer was extracted with EtOAc (20 mL). The combined organic layers were washed with sat. aq. NaCl and dried over anhydrous sodium sulfate. Concentration afforded an oily residue that was purified by flash column chromatography ($SiO_2$), eluting with a gradient of EtOAc to 10% MeOH in EtOAc to yield the intermediate acetamide (0.055 g, 75%, confirmed by MS), which was immediately dissolved in MeOH (6 mL). $K_2CO_3$ (0.023 g, 0.167 mmol) was added, and the mixture was heated to vigorous reflux for 1 h 45 min. The mixture was cooled, concentrated, and the residue was partitioned between EtOAc and 1:1 $H_2O$/sat. aq. NaCl (15 mL: 5 mL). The layers were separated, and the aqueous layer was extracted with EtOAc (5 mL). The combined organic layers were dried over anhydrous sodium sulfate and concentrated to yield a sticky residue that was diluted with $CH_2Cl_2$ (5 mL), and filtered to remove particulate matter. Methanolic HCl (~1.4 M, 2 mL) was added, the mixture was stirred for 10 min, and ether (25 mL) was added slowly until a whitish precipitate formed. This solid was collected and dried to afford the title compound as a cream-colored amorphous solid (0.052 g, 65% based on 29): mp 278-279° C. $^1H$-NMR (500 MHz; DMSO-$d_6$): δ 14.36 (s, 1 H), 9.65 (s, 2 H), 9.20 (br s, 1 H), 8.36 (d, J=9.3 Hz, 1 H), 8.25 (br s, 1 H), 7.91 (d, J=8.2 Hz, 1 H), 7.59 (s, 1 H), 7.51 (m, J=5.0 Hz, 2 H), 7.44-7.39 (m, 2 H), 7.30-7.26 (m, 1 H), 7.09 (d, J=9.3 Hz, 1 H), 4.22 (s, 2 H), 3.22 (br s, 4 H); $^{13}C$-NMR (126 MHz; DMSO-$d_6$): δ (162.9+160.9, 1 C), 154.3 (1 C), 142.8 (1 C), 142.4 (1 C), 135.9 (1 C), (134.63+134.57, 1 C), (130.76+130.70, 1 C), 129.1 (1 C), (126.24+126.22, 1 C), 125.8 (1 C), 119.8 (1 C), 117 (1 C), (116.96+116.79, 1 C), (115.90+115.73, 1 C), 113.4 (1 C), 49.2 (1 C), 47.1 (1 C), 31.6 (1 C); ESIMS m/z (rel. intensity) 296 (MH$^+$, 100); HRMS calcd for $C_{18}H_{18}FN_3$: 295.1485. found: 295.1487.

Example 13

7-[(3-Fluorophenethylamino)ethyl]quinolin-2-amine Dihydrochloride (7). To a solution of 29 (0.74 g, 0.321 mmol) in 7:1 CHCl$_3$/MeOH (8 mL), aldehyde 35 (0.052 g, 0.375 mmol) was added, followed by glacial AcOH (7 μL) and anhydrous MgSO$_4$ (approx. 0.5 g). The mixture was stirred at room temperature for 30 min and then cooled to 0° C. Sodium triacetoxyborohydride (0.079 g, 0.375 mmol) was added in one portion, and the mixture was slowly warmed to room temperature over 45 min, stirred 15 min at room temperature, and diluted with CHCl$_3$ (30 mL). The mixture was filtered, the filtrate was washed with sat. aq. NaHCO$_3$ (10 mL), and the aqueous layer was extracted with CHCl$_3$ (5 mL). The combined organic layers were washed with sat aq. NaCl (10 mL) and dried over anhydrous sodium sulfate. The solution was concentrated and the residue was purified by flash column chromatography (SiO$_2$), eluting with a gradient of EtOAc to 18% MeOH in EtOAc to yield the intermediate acetamide as a sticky syrup (0.030 g, 25%), which was immediately dissolved in MeOH (4 mL). K$_2$CO$_3$ (0.023 g, 0.163 mmol) was added, and the mixture was heated to vigorous reflux for 2 h. The mixture was cooled, concentrated, and the residue was partitioned between EtOAc and 3:2 H$_2$O/sat. aq. NaCl (10 mL: 5 mL). The layers were separated, and the aqueous layer was extracted with EtOAc (2 mL). The combined organic layers were washed with sat. NaCl (4 mL), dried over anhydrous sodium sulfate, and concentrated to yield a sticky residue that was diluted with CH$_2$Cl$_2$ (4 mL), and filtered to remove particulate matter. Methanolic HCl (~1.4 M, 2 mL) was added, the mixture was stirred for 10 min, and ether (20 mL) was added slowly and the mixture was sonicated until a whitish precipitate formed. This solid was collected and dried to afford the title compound as a hygroscopic, cream-colored amorphous solid (0.023 g, 18% based on 29): mp 247-249° C. (dec). $^1$H-NMR (500 MHz; DMSO-d$_6$): δ 14.34 (s, 1 H), 9.21 (br s, 3 H), 8.37 (d, J=9.3 Hz, 1 H), 8.27 (br s, 1 H), 7.92 (d, J=8.2 Hz, 1 H), 7.60 (s, 1 H), 7.43-7.38 (m, 2 H), 7.18-7.08 (m, 4 H), 3.25-3.16 (m, 6 H), 3.02 (t, J=8.1 Hz, 2 H). $^{13}$C-NMR (126 MHz; DMSO-d$_6$): δ (163.7+161.8, 1 C), 154.8 (1 C), 143.3 (1 C), 142.9 (1 C), (140.55+140.49, 1 C), 136.4 (1 C), (131.07+131.00, 1 C), 129.6 (1 C), 126.3 (1 C), (125.35+125.33, 1 C), 120.2 (1 C), 117.5 (1 C), (116.03+115.86 1 C), (114.19+114.02, 1 C), 113.86 (1 C), 47.7 (1 C), 32.1 (1 C), 31.6 (1 C); ESIMS m/z (rel. intensity) 310 (MH$^+$, 65); HRMS calcd for $C_{19}H_{20}FN_3$: 309.1641. found: 309.1645.

Example 14

3-Chlorophenylacetaldehyde (37). Dess-Martin periodinane (1.02 g, 2.4 mmol) was diluted in anhydrous CH$_2$Cl$_2$ (25 mL) under argon, and when solution was affected, 3-chlorophenethyl alcohol (33, 0.313 g, 2.00 mmol) was added dropwise. The mixture was stirred for 2 h and 15 min at room temperature, and was then quenched by addition of 20 mL sat. aq. Na$_2$S$_2$O$_3$. After stirring at room temperature for 15 min, the layers were separated, and the aqueous layer was extracted with CH$_2$Cl$_2$ (2×50 mL). The organic layer was washed with H$_2$O and sat. aq. NaCl (50 mL each) and was dried over anhydrous sodium sulfate and concentrated. The resulting semisolid residue was triturated with 10% EtOAc in hexanes, and the solid was filtered out and discarded. The filtrate was concentrated, and the oily residue was purified by flash column chromatography (SiO$_2$), eluting with a gradient of hexanes to 10% EtOAc in hexanes to afford the title compound as a clear yellow volatile oil (0.241 g, 78%). $^1$H-NMR (500 MHz; CDCl$_3$): δ 9.75 (t, J=2.1 Hz, 1 H), 7.31-7.23 (m, 3 H), 7.11-7.09 (m, 1 H), 3.69 (d, J=2.1 Hz, 2 H).

Example 15

4-Chlorophenylacetaldehyde (38). Dess-Martin periodinane (1.02 g, 2.4 mmol) was diluted in anhydrous CH$_2$Cl$_2$ (25 mL) under argon, and when solution was affected, 4-chlorophenethyl alcohol (33, 0.313 g, 2 mmol) was added dropwise. The mixture was stirred for 2 h and 15 min at room temperature, and was then quenched by addition of 20 mL sat. aq. Na$_2$S$_2$O$_3$. After stirring at room temperature for 15 min, the layers were separated, and the aqueous layer was extracted with CH$_2$Cl$_2$ (2×50 mL). The organic layer was washed with H$_2$O and sat. aq. NaCl (50 mL each) and was dried over anhydrous sodium sulfate and concentrated. The resulting semisolid residue was triturated with 10% EtOAc in hexanes, and the solid was filtered and discarded. The filtrate was concentrated, and the oily residue was purified by flash column chromatography (SiO$_2$), eluting with a gradient of hexanes to 15% EtOAc in hexanes to afford the title compound as a clear yellow volatile oil (0.211 g, 88%). $^1$H-NMR (500 MHz; CDCl$_3$): δ 9.75 (t, J=2.1 Hz, 1 H), 7.34 (d, J=8.3 Hz, 2 H), 7.15 (d, J=8.2 Hz, 2 H), 3.69 (d, J=2.0 Hz, 2 H).

Example 16

7-[(4-Fluorophenethylamino)ethyl]quinolin-2-amine Dihydrochloride (14). Compound 29 (0.076 g, 0.333 mmol) was diluted in 7:1 CHCl$_3$:MeOH (7 mL), and aldehyde 36 (0.045 g, 0.327 mmol) was added as a solution in 1 mL CHCl$_3$, followed by glacial acetic acid (7 μL) and anhydrous MgSO$_4$ (~0.5 g). The flask was sheathed with aluminum foil, and the mixture was stirred for 45 min, cooled to 0° C., and sodium triacetoxyborohydride (0.085 g, 0.401 mmol) was added in one portion. The mixture was allowed to warm to room temperature slowly over 1 h and 15 min and was diluted with CHCl$_3$ (to a volume of approximately 50 mL) and filtered. The yellow filtrate was washed with sat. aq. NaHCO$_3$ (10 mL) and the aqueous layer was extracted with CHCl$_3$ (2×5 mL). The organic phase was washed with sat. aq. NaCl (20 mL), dried over anhydrous sodium sulfate, and concentrated. The resulting residue was purified by flash column chromatography (SiO$_2$) eluting with a gradient of EtOAc to 14% MeOH in EtOAc to yield the intermediate acetamide (0.051 g, 44%) as an oil that began to solidify on standing. This substance was immediately diluted with anhydrous MeOH (8 mL), and K$_2$CO$_3$ (0.030 g, 0.217 mmol) was added. The mixture was heated at reflux for 2 h, cooled, and concentrated. The residue was diluted with EtOAc (10 mL) and the solution was washed with H$_2$O: sat. aq. NaCl (1:1, 6 mL). The aqueous layer was extracted with EtOAc (3×6 mL), and the combined organic layers were washed with sat. aq. NaCl (6 mL), dried over anhydrous sodium sulfate, and concentrated. The resulting syrup was diluted in CH$_2$Cl$_2$ (5 mL) filtered to remove particulate matter, and reconcentrated. To the residue was added methanolic HCl (~1.4 M, 1 mL), and the mixture was stirred at room temperature for 1 h, upon which a white crystalline solid formed. The mixture was cooled to −30° C. and filtered to yield the title compound as white flocculent crystals (0.021 g, 16% from 29): mp 279-281° C. $^1$H-NMR (500 MHz; DMSO-d$_6$): δ 14.34 (s, 1 H), 9.20 (s, 3 H), 8.37 (d, J=9.3 Hz, 1 H), 8.26-8.24 (br s, 1 H), 7.92 (d, J=8.2 Hz, 1 H), 7.60 (s, 1 H), 7.42 (dd, J=8.2, 1.2 Hz, 1 H), 7.33 (td, J=6.1, 2.5 Hz, 2 H), 7.21-7.17 (m, 2 H), 7.09 (d, J=9.3 Hz, 1 H), 3.26-3.16 (m, 6 H), 2.98 (t, J=8.1 Hz, 2 H); $^{13}$C-NMR (126 MHz; DMSO-d$_6$): δ (162.1+160.2 1 C), 154.3 (1 C), 142.8 (1 C), 142.4 (1C), 135.9 (1 C), (133.34+133.32, 1 C), (130.59+130.53, 1 C), 129.1 (1 C), 125.8 (1 C), 119.7 (1 C), 117.0 (1 C), (115.45+115.28, 1 C), 113.4 (1 C), 47.7 (1 C), 47.2 (1 C), 31.7 (1 C), 30.7 (1 C); ESIMS m/z (rel. intensity) 310 (MH$^+$, 100); HRMS calcd for C$_{19}$H$_{20}$FN$_3$: 309.1641. found: 309.1644.

Example 17

7-[(3-Chlorophenethylamino)ethyl]quinolin-2-amine Dihydrochloride (15). Compound 29 (0.076 g, 0.333 mmol) was diluted in 8:1 CHCl$_3$:MeOH (7 mL), and aldehyde 37 (0.051 g, 0.330 mmol) was added as a solution in 1 mL CHCl$_3$, followed by glacial acetic acid (7 μL) and anhydrous MgSO$_4$ (~0.5 g). The mixture was stirred for 30 min, cooled to 0° C., and sodium triacetoxyborohydride (0.085 g, 0.401 mmol) was added in one portion. The mixture was allowed to warm to room temperature slowly over 1 h and was diluted with CHCl$_3$ (to a volume of approximately 50 mL) and filtered. The yellow filtrate was washed with sat. aq. NaHCO$_3$ (10 mL) and the aqueous layer was extracted with CHCl$_3$ (10 mL). The organic phase was washed with sat. aq. NaCl (20 mL), dried over anhydrous sodium sulfate, and concentrated. The resulting residue was purified by flash column chromatography (SiO$_2$) eluting with a gradient of EtOAc to 13% MeOH in EtOAc to yield the intermediate acetamide (0.039 g, 32%) as a semisolid. This substance was diluted with anhydrous MeOH (6 mL) and K$_2$CO$_3$ (0.029 g, 0.210 mmol) was added. The mixture was heated at reflux for 2 h, cooled, and concentrated. The residue was immediately diluted with EtOAc (10 mL) and the solution was washed with H$_2$O: sat. aq. NaCl (3:5, 8 mL). The organic layers were washed with sat. aq. NaCl (5 mL), dried over anhydrous sodium sulfate, and concentrated. The resulting syrup was diluted in CH$_2$Cl$_2$ (5 mL) filtered to remove particulate matter, and reconcentrated. To the residue was added methanolic HCl (~1.4 M, 3 mL) and the mixture was stirred at room temperature for 5 min, and ether (20 mL) was added, upon which an off-white solid (0.030 g, 23%) was collected. An analytically pure sample for assay was prepared by preparative LC-MS, using the instrument and column detailed in the General Procedures section, eluting with a gradient of 95% H$_2$O+0.1%/formic acid 5% MeCN+0.1% formic acid for 2 min, to 70% H$_2$O at 27 min, then to 0% H$_2$O at 32 min. Evaporation and re-treatment of the residue with methanolic HCl (1 mL) and ether (1 mL) afforded the pure compound as a white flocculent solid (0.014 g, 11% from 29): mp 281-282° C. $^1$H-NMR (500 MHz; DMSO-d$_6$): δ 14.29 (s, 1 H), 9.17 (br s, 3 H), 8.37 (d, J=9.3 Hz, 1 H), 8.25 (br s, 1 H), 7.92 (d, J=8.2 Hz, 1 H), 7.60 (s, 1 H), 7.44-7.34 (m, 4 H), 7.27 (d, J=7.4 Hz, 1 H), 7.09 (d, J=9.3 Hz, 1 H), 3.25-3.20 (m, 4 H), 3.20-3.16 (m, 2 H), 3.00 (t, J=8.1 Hz, 2 H); $^{13}$C-NMR (126 MHz; DMSO-d$_6$): δ 154.3 (1 C), 142.8 (1 C), 142.5 (1 C), 139.8 (1 C), 135.8 (1 C), 133.2 (1 C), 130.5 (1 C), 129.1 (1 C), 128.6 (1 C), 127.5 (1 C), 126.8 (1 C), 125.8 (1 C), 119.7 (1 C), 116.9 (1 C), 113.4 (1 C), 47.2 (1 C), 31.6 (1 C), 31.0 (1 C); ESIMS m/z (rel. intensity) 326 (MH$^+$, 100); HRMS calcd for C$_{19}$H$_{20}$ClN$_3$: 325.1346. found: 325.1352.

Example 18

7-[(4-Chlorophenethylamino)ethyl]quinolin-2-amine Dihydrochloride (16). Compound 29 (0.076 g, 0.333 mmol) was diluted in 7:1 CHCl$_3$:MeOH (7 mL), and aldehyde 38 (0.051 g, 0.330 mmol) was added as a solution in 1 mL CHCl$_3$, followed by glacial acetic acid (7 μL) and anhydrous MgSO$_4$ (~0.5 g). The mixture was stirred for 30 min, cooled to 0° C., and sodium triacetoxyborohydride (0.085 g, 0.401 mmol) was added in one portion. The mixture was allowed to warm to room temperature slowly over 1 h 15 min, and was diluted with CHCl$_3$ (to a volume of approximately 50 mL) and filtered. The yellow filtrate was washed with sat. aq. NaHCO$_3$ (10 mL), and the aqueous layer was extracted with CHCl$_3$ (2×5 mL). The organic phase was washed with sat. aq. NaCl (20 mL), dried over anhydrous sodium sulfate, and concentrated. The resulting residue was purified by flash column chromatography (SiO$_2$) eluting with a gradient of EtOAc to 13% MeOH in EtOAc) to yield the intermediate acetamide (0.032 g, 26%) as a white semisolid. This substance was immediately diluted with anhydrous MeOH (7 mL), and K$_2$CO$_3$ (0.024 g, 0.174 mmol) was added. The mixture was heated at reflux for 2 h, cooled, and concentrated. The residue was diluted with EtOAc (10 mL), and the solution was washed with H$_2$O: sat. aq. NaCl (3:5, 8 mL). The organic layers were washed with sat. aq. NaCl (5 mL), dried over anhydrous sodium sulfate, and concentrated. The resulting syrup was diluted in CH$_2$Cl$_2$ (5 mL) filtered to remove particulate matter, and reconcentrated. To the residue was added methanolic HCl (~1.4 M, 3 mL), the mixture was stirred at room temperature for 5 min, and ether (20 ml) was added, upon which an off-white solid (0.027 g, 20%) was collected. An analytically pure sample for assay was prepared by preparative LC-MS, using the instrument and column detailed in the General Procedures section, eluting with a gradient of 95% H$_2$O+0.1% formic acid/5% MeCN+0.1% formic acid for 5 min, to 93% H$_2$O in 30 min, then to 0% H$_2$O at 32 min. Evaporation and re-treatment of the residue with methanolic HCl (1 mL) and ether (1 mL) afforded the pure compound as a white flocculent solid (0.0094 g, 7.4% from 29): mp 288-290° C. (dec). $^1$H-NMR (500 MHz; DMSO-d$_6$): δ 14.20 (s, 1 H), 9.07 (s, 3 H), 8.36 (dd, J=9.2, 0.5 Hz, 1 H), 8.22 (br s, 1 H), 7.91 (d, J=8.1 Hz, 1 H), 7.58 (s, 1 H), 7.44-7.41 (m, 3 H), 7.32 (d, J=8.4 Hz, 2 H), 7.07 (d, J=9.2 Hz, 1 H), 3.28-3.14 (m, 6 H), 2.97 (t, J=8.1 Hz, 2 H); $^{13}$C-NMR (126 MHz; DMSO-d$_6$): δ 154.4 (1 C), 142.8 (1 C), 142.4 (1 C), 136.2 (1 C), 131.4 (1 C), 130.6 (1 C), 129.1 (1 C), 28.6 (1 C), 125.8 (1 C), 119.8 (1 C), 117.0 (1 C), 113.4 (1 C), 47.40 (1 C), 47.22 (1 C), 31.7 (1 C), 30.8 (1 C); one of the aniinoquinoline carbons is not visible due to line-broadening. ESIMS m/z (rel. intensity) 326 (MH$^+$, 30); HRMS calcd for C$_{19}$H$_{20}$ClN$_3$: 325.1346. found: 325.1353.

Example 19

3-Fluorophenyl-1-propanol (40). 3-Fluorophenylpropionic acid (39, 0.500 g, 2.97 mmol) was diluted in anhydrous THF (2 mL) under argon, and cooled to 0° C. Borane-THF (1 M, 4.16 mL, 4.16 mmol) was added dropwise, and the mixture was allowed to warm to room temperature and stirred for 18 h. The reaction was quenched by the addition of 1:1 THF/H$_2$O (5 mL). When gas evolution ceased, solid K$_2$CO$_3$ was added until the mixture separated into two layers, which were separated. The aqueous layer was extracted with EtOAc (2×5 mL), and the combined organic layers were washed with H$_2$O (15 mL) and sat. aq. NaCl (15 mL), dried over anhydrous sodium sulfate, and concentrated to yield the product as a clear oil (0.446 g, 97%) after drying in vacuo. $^1$H-NMR (500 MHz; CDCl$_3$): δ 7.29-7.25 (m, 1 H), 7.00 (d, J=7.6 Hz, 1 H), 6.95-6.89 (m, 2 H), 3.71 (t, J=6.4 Hz, 2 H), 2.74 (t, J=7.7 Hz, 2 H), 1.95-1.89 (m, 2 H), 1.39 (s, 1 H).

Example 20

3-Fluorophenyl-1-propanal (41). Anhydrous $CH_2Cl_2$ (10 mL) was cooled to −78° C., and anhydrous DMSO (0.546 g, 7.00 mmol) was added, followed, dropwise, by oxalyl chloride (0.380 g, 3.00 mmol). Once gas evolution ceased, compound 40 (0.308 g, 2 mmol) was added dropwise and the resulting milky solution was stirred for 15 min. $Et_3N$ (1.17 mL, 8.4 mmol) was added slowly and the mixture was stirred for 15 min at −78° C. and then warmed to room temperature and stirred for 1 h. The yellow mixture was diluted with $H_2O$ (30 mL) and the layers were separated. The aqueous layer was extracted with $CH_2Cl_2$ (2×15 mL), and the organic layers were washed with $H_2O$ and sat. aq. NaCl (15 mL each). The solution was dried over anhydrous sodium sulfate, concentrated, and the resulting residue was purified by flash column chromatography ($SiO_2$), eluting with a gradient of hexanes to 10% EtOAc in hexanes to yield the title aldehyde as a colorless volatile oil (0.220 g, 72%). $^1$H-NMR (500 MHz; $CDCl_3$): δ 9.82 (s, 1 H), 7.27-7.23 (m, 1 H), 6.97 (d, J=7.6 Hz, 1 H), 6.92-6.89 (m, 2 H), 2.96 (t, J=7.5 Hz, 2 H), 2.81-2.78 (m, 2 H).

Example 21

7-{2-[3-(3-Fluorophenyhpropylamino)ethyl]}quinolin-2-amine Dihydrochloride (8). Compound 29 (0.064 g, 0.280 mmol) was diluted in 7:1 $CHCl_3$: MeOH (7 mL), and aldehyde 41 (0.049 g, 0.322 mmol) was added, followed by glacial acetic acid (6 μL) and anhydrous $MgSO_4$ (~0.5 g). The mixture was stirred for 30 min, cooled to 0° C., and sodium triacetoxyborohydride (~0.070 g, 0.333 mmol) was added in one portion. The mixture was allowed to warm to room temperature slowly over 50 min and was diluted with $CHCl_3$ (to a volume of approximately 50 mL) and filtered. The yellow filtrate was washed with sat. aq. $NaHCO_3$ (8 mL) and the aqueous layer was extracted with $CHCl_3$ (5 mL). The organic phase was washed with sat. aq. NaCl (10 mL), dried over anhydrous sodium sulfate, and concentrated. The resulting residue was purified by flash column chromatography ($SiO_2$) eluting with a gradient of EtOAc to 17% MeOH in EtOAc to yield the intermediate acetamide (0.045 g, 44%) as a sticky semisolid. This substance was immediately diluted with anhydrous MeOH (6 mL) and $K_2CO_3$ (0.034 g, 0.246 mmol) was added. The mixture was heated at reflux for 1 h 50 min, cooled, and concentrated. The residue was diluted with EtOAc (10 mL), and the solution was washed with $H_2O$: sat. aq. NaCl (1:1, 6 mL). The organic layers were washed with sat. aq. NaCl (5 mL), dried over anhydrous sodium sulfate, and concentrated. The resulting syrup was diluted in $CH_2Cl_2$ (3 mL), filtered to remove particulate matter, methanolic HCl added (~1.4 M, 3 mL), and the mixture stirred at room temperature for 10 min. Ether (30 mL) was added, and the mixture was sonicated, concentrated, and the residue was washed twice with ether (2 mL each) to afford the product as a cream-colored hygroscopic solid (0.042 g, 37% from 29): mp 81-83° C. (softens), 210° C. (dec). $^1$H-NMR (500 MHz; DMSO-$d_6$): δ 14.31 (s, 1 H), 9.21-9.13 (m, 3 H), 8.37 (d, J=9.3 Hz, 1 H), 8.25 (br s, 1 H), 7.91 (d, J=8.2 Hz, 1 H), 7.59 (s, 1 H), 7.42 (dd, J=8.2, 1.3 Hz, 1 H), 7.38-7.34 (m, 1 H), 7.12-7.03 (m, 4 H), 3.21-3.14 (m, 4 H), 2.95-2.90 (m, 2 H), 2.71 (t, J=7.6 Hz, 2 H), 1.96 (dt, J=15.3, 7.7 Hz, 2 H); $^{13}$C-NMR (126 MHz; DMSO-$d_6$): δ (163.2+161.3, 1 C), 154.3 (1 C), (143.71+143.65, 1 C), 142.8 (1 C), 142.5 (1 C), 135.8 (1 C), (130.32+130.25, 1 C), 129.1 (1 C), 125.8 (1 C), (124.47+124.45, 1 C), 119.7 (1 C), 117.0 (1 C), (115.09+114.92, 1 C), 113.4 (1 C), (112.95+112.79, 1 C), 47.1 (1 C), 46.1 (1 C), 31.73 (1 C), 31.54 (1 C), 26.8 (1 C); ESIMS m/z (rel. intensity) 324 (MH$^+$, 28); HRMS calcd for $C_{20}H_{22}FN_3$: 323.1798. found: 323.1800.

Example 22

2-Chloro-6-Methylquinoline (44). Compound 42 (3.75 g, 15.8 mmol) was diluted in chlorobenzene (40 mL), and aluminum chloride (10.5 g, 75.0 mmol) was added. The mixture was heated to 90° C. under nitrogen for 2 h, upon which the mixture became black, was subsequently cooled, and poured into ice-$H_2O$ (300 g). The resulting suspension was extracted with EtOAc (700 mL), and the organic layer was washed with $H_2O$ (300 mL) and dried over anhydrous sodium sulfate. Concentration afforded an orange solid that was recrystallized from hot MeOH (60 mL) to yield an orange iridescent solid (1.95 g, 77%). This was not characterized, but was instead diluted in $POCl_3$ (30 mL) and heated at reflux for 70 min before cooling and pouring into ice-$H_2O$ (400 mL) in a large beaker. The beaker was immersed in a cooler of ice, with stirring, and solid NaOH was added until the pH was approximately 7. The oily suspension was extracted with EtOAc (400 mL), washed with sat. aq. NaCl (300 mL), and the organic layer was dried over anhydrous sodium sulfate. The solution was concentrated to yield a solid that was purified by flash column chromatography ($SiO_2$), eluting with a gradient of hexanes to 40% EtOAc in hexanes to yield the product as an orange crystalline solid (1.79 g, 64% from 42). The $^1$H NMR chemical shifts for this compound are identical to those previously reported by Inglis et al. $^1$H-NMR (500 MHz; $CDCl_3$): δ 8.01 (d, J=8.6 Hz, 1 H), 7.91 (d, J=9.2 Hz, 1 H), 7.57-7.55 (m, 2 H), 7.34 (d, J=8.6 Hz, 1 H), 2.53 (s, 3 H).

Example 23

2-(Acetamido)-6-methylquinoline (45). Chloride 44 (0.300 g, 1.69 mmol) was diluted with molten anhydrous acetamide (8 g, 135 mmol), and $K_2CO_3$ (1.17 g, 8.45 mmol) was added. The mixture was heated in a sand bath, at reflux (~230° C.) for 16 h. The mixture was cooled, poured into $H_2O$ (120 mL) and extracted with EtOAc (4×30 mL). The organic layers were washed with $H_2O$ (3×100 mL) and sat. aq. NaCl (50 mL) and dried over anhydrous sodium sulfate and concentrated. Purification of the residue by flash column chromatography ($SiO_2$), eluting with a gradient of 10% EtOAc in $CH_2Cl_2$ to 30% EtOAc in $CH_2Cl_2$ afforded the desired compound as a white solid (0.250 g, 74%). $^1$H NMR chemical shifts for this compound are consistent with those reported in the literature. $^1$H-NMR (500 MHz; $CDCl_3$): δ 8.36 (br d, J=8.6 Hz, 1 H), 8.27 (br s, 1 H), 8.09 (d, J=8.9 Hz, 1 H), 7.70 (d, J=8.6 Hz, 1 H), 7.55 (s, 1 H), 7.50 (dd, J=8.6, 1.9 Hz, 1 H), 2.51 (s, 3 H), 2.24 (s, 3 H).

Example 24

2-(Acetamido)-6-(bromomethyl)quinoline (46). Compound 45 (0.300 g, 1.50 mmol) was diluted in anhydrous benzene (10 mL). N-Bromosuccinimide (0.280 g, 1.57 mmol) and a catalytic amount (~0.020 g) of benzoyl peroxide were added, and the mixture was heated to reflux under nitrogen until an orange tint was no longer visible in the solution refluxing in the condenser (around 2 h 40 min). The mixture was cooled, concentrated, and purified by flash column chromatography ($SiO_2$), eluting with a gradient of 10% to 12% EtOAc in $CH_2Cl_2$ to yield the product (0.262 g, 63%) as a flocculent yellow solid. The $^1$H NMR chemical shifts for this compound are identical to those previously reported in the literature. $^1$H-NMR (500 MHz; CDCl$_3$): δ 8.44 (br d, J=8.6 Hz, 1 H), 8.30 (br s, 1 H), 8.17 (d, J=9.0 Hz, 1 H), 7.82 (m, J=9.1 Hz, 2 H), 7.72 (dd, J=8.6, 2.1 Hz, 1 H), 4.67 (s, 2 H), 2.29 (s, 3 H).

Example 25

6-[(3-Fluorophenethylamino)methyl]quinolin-2-amine Dihydrochloride (10). Anhydrous Cs$_2$CO$_3$ (0.090 g, 0.288 mmol) was diluted in anhydrous DMF (5 mL), and amine 22 (0.040 g, 0.288 mmol) was added. The mixture was stirred for 30 min at room temperature before compound 46 (0.070 g, 0.250 mmol) was added dropwise as a solution in anhydrous DMF (2 mL). The resultant suspension was stirred for 16 h at room temperature and concentrated, and the residue was partitioned between EtOAc and H$_2$O (5 mL each), and the layers were separated. The aqueous layer was extracted with EtOAc (2×5 mL), and the organic layers were washed with sat. aq. NaCl (5 mL), dried over anhydrous sodium sulfate, and concentrated. The residue was purified by flash column chromatography (SiO$_2$), eluting with a gradient of EtOAc to 10% MeOH in EtOAc to yield the intermediate acetamide as a yellow syrup (0.040 g, 47%, confirmed by MS). This syrup was dissolved in MeOH (5 mL), and K$_2$CO$_3$ (0.026 g, 0.148 mmol) was added. The mixture was heated at reflux for 2 h, cooled to room temperature, and concentrated. The residue was partitioned between EtOAc (5 mL) and sat. aq. NaCl: H$_2$O (4:1, 5 mL). The layers were separated and the aqueous layer was extracted with EtOAc (2×5 mL). The combined organic phase was washed with sat aq. NaCl (4 mL), dried over anhydrous sodium sulfate, and concentrated. The resulting residue was diluted in CH$_2$Cl$_2$ (5 mL), filtered to remove particulate matter, and methanolic HCl (~1.4 M, 3 mL) was added. After 10 min, ether (20 mL) was added, and a precipitate formed. This was collected and dried to yield the title compound as a cream-colored powder (0.036 g, 38% from 46: mp 277-278° C. $^1$H-NMR (500 MHz; DMSO-d$_6$): δ 14.35 (s, 1 H), 9.58 (s, 2 H), 9.28 (br s, 1 H), 8.37 (d, J=9.5 Hz, 1 H), 8.32 (br s, 1 H), 8.05 (s, 1 H), 7.96 (d, J=8.6 Hz, 1 H), 7.78 (d, J=8.5 Hz, 1 H), 7.39 (td, J=7.8, 6.4 Hz, 1 H), 7.16-7.09 (m, 4 H), 4.29 (s, 2 H), 3.20-3.19 (m, 2 H), 3.05 (t, J=8.1 Hz, 2 H); $^{13}$C-NMR (126 MHz; DMSO-d$_6$): δ (163.2+161.2, 1 C), 154.4 (1 C), 142.8 (1 C), (140.11+140.05, 1 C), 135.9 (1 C), 134.2 (1 C), 130.59 (1 C), (130.58+130.52, 1 C), 128.6 (1 C), (124.83+124.81, 1 C), 120.5 (1 C), 117.6 (1 C), (115.53+115.36, 1 C) 114.5 (1 C), (113.69+113.52, 1 C), 49.2 (1 C), 47.0 (1 C), 31.0 (1 C); ESIMS m/z (rel. intensity) 296 (MH$^+$, 100); HRMS calcd for C$_{18}$H$_{18}$FN$_3$: 295.1485. found: 295.1490.

Example 26

2-(Acetamido)-6-(cyanomethyl)quinoline (47). Compound 46 (0.254 g, 0.91 mmol) was diluted with anhydrous DMF (10 mL), and NaCN (0.230 g, 4.55 mmol) was added. The orange mixture was stirred at room temperature for 17 h. The mixture was concentrated and partitioned between EtOAc and H$_2$O (50 mL each) and the layers were separated. The aqueous phase was extracted with EtOAc (2×50 mL) and the combined organic layers were washed with H$_2$O (2×80 mL) and sat aq. NaCl (50 mL), and dried over anhydrous sodium sulfate and concentrated. The residue was purified by flash column chromatography (SiO$_2$), eluting with a gradient of 15% EtOAc in CH$_2$Cl$_2$ to 25% EtOAc in CH$_2$Cl$_2$ to yield the title compound as a white solid (0.170 g, 83%): mp 154-155° C.; $^1$H-NMR (500 MHz; CDCl$_3$): δ 8.48 (d, J=8.6 Hz, 1 H), 8.22 (br s, 1 H), 8.20 (d, J=9.0 Hz, 1 H), 7.85 (d, J=8.7 Hz, 1 H), 7.81 (d, J=1.0 Hz, 1 H), 7.61 (dd, J=8.7, 2.1 Hz, 1 H), 3.96 (s, 2 H), 2.30 (s, 3 H); $^{13}$C-NMR (126 MHz; CDCl$_3$): δ 169.1 (1 C), 151.3 (1 C), 145.8 (1 C), 138.6 (1 C), 129.8 (1 C), 128.3 (1 C), 126.74 (1 C), 126.64 (1 C), 126.2 (1 C), 117.6 (1 C), 114.9 (1 C), 25.0 (1 C), 23.7 (1 C); ESIMS m/z (rel. intensity) 472 (2M+Na$^+$, 100).

Example 27

2-(Acetamido)-6-(2-aminoethyl)quinoline (48). Compound 47 (0.060 g, 0.266 mmol) was diluted in absolute EtOH (7 mL) and methanolic ammonia (7 N, 7 mL) was added. Raney nickel (~1.5 g, washed with H$_2$O and MeOH) was added, and the mixture was degassed and hydrogenated with a balloon at room temperature for 30 min while stirring rapidly. The clear solution was decanted away from the nickel and was filtered through a Pall 0.2 μm syringe filter to remove fine particulate matter. The solution was concentrated and dried in vacuo to yield a colorless gum that became a white semisolid upon standing (0.050 g, 82%). Conversion to this amine was confirmed by $^1$H NMR spectrometry, TLC, MS, and ninhydrin staining, and it was used crude without any further characterization or purification.

Example 28

6-[2-(3-Fluorobenzylamino)ethyl]quinolin-2-amine Dihydrochloride (11). Amine 48 (0.050 g, 0.218 mmol) was dissolved in anhydrous CHCl$_3$ (3 mL), and aldehyde 30 (0.034 g, 0.274 mmol) was added, followed by 3 mL of a 2:1 mixture of CHCl$_3$:MeOH and anhydrous sodium sulfate (~0.5 g). The mixture was stirred rapidly at room temperature for 90 min, after which glacial acetic acid (10 μL) was added. After a total of 4 h, the amine appeared consumed by TLC, and the mixture was filtered to remove the sodium sulfate. The filtrate was concentrated, and the oily residue was diluted in MeOH (5 mL). NaBH$_4$ (0.020 g, 0.523 mmol) was added and the mixture was stirred for 40 minutes at room temperature. The mixture was concentrated and partitioned between EtOAc and H$_2$O (10 mL of each). The layers were separated, and the aqueous layer was extracted with EtOAc (10 mL). The organic layer was washed with H$_2$O and sat aq. NaCl (20 mL each), dried over anhydrous sodium sulfate, and concentrated. The residue was purified by flash column chromatography (SiO$_2$), eluting with a gradient of EtOAc to 20% MeOH in EtOAc to yield the intermediate acetamide as a yellow syrup (0.052 g, 72%, confirmed by MS). This compound was immediately diluted in MeOH (5 mL), and K$_2$CO$_3$ (0.021 g, 0.154 mmol) was added. The mixture was heated at vigorous reflux for 2 h, cooled, concentrated, and the resulting residue was diluted with EtOAc (20 mL) and washed with H$_2$O (10 mL). The aqueous layer was extracted with EtOAc (2×10 mL), and the combined organic layers were washed with sat. aq. NaCl (10 mL) and dried over anhydrous sodium sulfate. Concentration afforded a white solid, which was diluted with methanolic HCl (~1.4 M, 3 mL) and stirred for 10 min. The addition of ether (50 mL) resulted in the precipitation of a solid that was collected, washed with ether (20 mL) and dried in vacuo to yield the title compound as a white solid (0.043 g, 54% from 48): mp 282-284° C. $^1$H-NMR (500 MHz; DMSO-d$_6$): δ 14.24 (s, 1 H), 9.62 (s, 2 H), 9.16 (br s, 1 H), 8.35 (d, J=9.4 Hz, 1 H), 8.19 (br s, 1 H), 7.80 (d, J=0.7 Hz, 1 H), 7.71-7.67 (m, 2 H), 7.52-7.48 (m, 2 H), 7.42 (d, J=7.7 Hz, 1 H), 7.30-7.26 (m, 1 H), 7.12 (d, J=9.3 Hz, 1 H), 4.22 (s, 2 H), 3.17-3.14 (m, 4 H); $^{13}$C-NMR (126 MHz; DMSO-d$_6$): δ

(162.9+160.9, 1 C), 154.0 (1 C), 142.8 (1 C), (134.62+134.56, 1 C), 134.0 (1 C), 133.3 (1 C), (130.76+130.70, 1 C), 128.3 (1 C), (126.24+126.22, 1 C), 121.0 (1 C), 117.7 (1 C), (116.96+116.79, 1 C), (115.90+115.74, 1 C), 114.0 (1 C), 49.2 (1 C), 47.2 (1 C), 30.8 (1 C); one of the aminoquinoline carbons is not visible because of baseline broadening; ESIMS m/z (rel. intensity) 296 (MH$^+$, 100); HRMS calcd for $C_{18}H_{18}FN_3$: 295.1485. found: 295.1486.

Example 29

6-[(3-Fluorophenethylamino)ethyl]quinolin-2-amine Dihydrochloride (12). To a solution of 48 (0.074 g, 0.321 mmol) in 7:1 CHCl$_3$/MeOH (8 mL), aldehyde 35 (0.049 g, 0.353 mmol) was added, followed by glacial AcOH (7 μL) and anhydrous MgSO$_4$ (approx 0.5 g). The mixture was stirred at room temperature for 20 min and then cooled to 0° C. Sodium triacetoxyborohydride (0.082 g, 0.385 mmol) was added in one portion, and the mixture was slowly warmed to room temperature over 50 min, then diluted with CH$_2$Cl$_2$ (10 mL). The mixture was filtered, the filtrate was washed with sat. aq. NaHCO$_3$ (2×20 mL), and the aqueous layer was extracted with CH$_2$Cl$_2$ (2×10 mL). The combined organic layers were washed with sat. aq. NaCl (10 mL) and dried over anhydrous sodium sulfate. The solution was concentrated, and the residue was purified by flash column chromatography (SiO$_2$), eluting with a gradient of EtOAc to 20% MeOH in EtOAc to yield the intermediate acetamide as a sticky syrup (0.039 g, 34%) that was immediately dissolved in MeOH (3 mL). K$_2$CO$_3$ (0.023 g, 0.167 mmol) was added, and the mixture was heated to vigorous reflux for 1 h 50 min. The mixture was cooled, concentrated, and the residue was partitioned between EtOAc (10 mL) and 1:1 H$_2$O/sat. aq. NaCl (4 mL). The layers were separated, and the aqueous layer was extracted with EtOAc (2×4 mL). The combined organic layers were washed with sat. aq. NaCl (4 mL), dried over anhydrous sodium sulfate, and concentrated to yield a sticky residue that was diluted with CH$_2$Cl$_2$ (3 mL), and filtered to remove particulate matter. Methanolic HCl (~1.4 M, 2 mL) was added, the mixture was stirred for 10 min and concentrated, and the residue was recrystallized from 1:1 MeOH/ether (1 mL) to yield the product as a pale tan hygroscopic solid (0.025 g, 21% based on 48): mp 223-226° C. (dec). $^1$H-NMR (500 MHz; DMSO-d$_6$): δ 14.37 (s, 1 H), 9.35-9.23 (m, 3 H), 8.36 (d, J=9.4 Hz, 1 H), 8.30 (br s, 1 H), 7.83 (s, 1 H), 7.73-7.69 (m, 2 H), 7.42-7.38 (m, 1 H), 7.18-7.09 (m, 4 H), 3.22-3.19 (m, 4 H), 3.14 (t, J=7.9 Hz, 2 H), 3.04 (t, J=8.1 Hz, 2 H); $^{13}$C-NMR (126 MHz; DMSO-d$_6$): δ (163.2+161.3, 1 C), 154.0 (1 C), 142.8 (1 C), (140.14+140.08, 1 C), 134.6 (1 C), 134.1 (1 C), 133.3 (1 C), (130.58+130.51, 1 C), 128.3 (1 C), (124.86+124.84, 1 C), 120.9 (1 C), 117.5 (1 C), (115.54+115.37, 1 C), 114.0 (1 C), (113.68+113.52, 1 C), 47.35 (1 C), 47.20 (1 C), 31.0 (1 C), 30.8 (1C); ESIMS m/z (rel. intensity) 310 (MH$^+$, 100); HRMS calcd for $C_{19}H_{20}FN_3$: 309.1641. found: 309.1647.

Example 30

6-{2-[3-(3-Fluorophenyhpropylamino)ethyl]}quinolin-2-amine Dihydrochloride (13). To a solution of 48 (0.060 g, 0.261 mmol) in 10:1 CHCl$_3$/MeOH (5 mL), aldehyde 41 (0.047 g, 0.313 mmol) was added, followed by glacial AcOH (6 μL) and anhydrous MgSO$_4$ (approx 0.5 g). The mixture was stirred at room temperature for 25 min and then cooled to 0° C. Sodium triacetoxyborohydride (0.070 g, 0.332 mmol) was added in one portion, and the mixture was slowly warmed to room temperature over 30 min, filtered, and concentrated. The residue was purified by flash column chromatography (SiO$_2$), eluting with a gradient of EtOAc to 20% MeOH in EtOAc to yield a sticky yellow solid (0.036 g, 27%). This substance was immediately dissolved in MeOH (3 mL), K$_2$CO$_3$ (0.030 g, 0.217 mmol) was added, and the mixture was heated to vigorous reflux for 2 h. The mixture was cooled, concentrated, and the residue was partitioned between EtOAc (6 mL) and 1:1 H$_2$O/sat. aq. NaCl (2 mL). The layers were separated, and the aqueous layer was extracted with EtOAc (2×3 mL). The combined organic layers were washed with sat. aq. NaCl (3 mL), dried over anhydrous sodium sulfate, and concentrated to yield a sticky residue that was diluted with CH$_2$Cl$_2$ (3 mL), and filtered to remove particulate matter. Methanolic HCl (~1.4 M, 2 mL) was added, the mixture was stirred for 10 min, concentrated, and the residue was washed with 1:1 CH$_2$Cl$_2$/ether (3 mL) to yield the product as a yellow-green hygroscopic solid (0.033 g, 32% based on 48): mp 70° C. (softens), 211-213° C. (dec). $^1$H-NMR (500 MHz; DMSO-d$_6$): δ 14.31 (s, 1 H), 9.20 (br s, 3 H), 8.34 (d, J=9.4 Hz, 1 H), 8.22 (br s, 1 H), 7.82 (s, 1 H), 7.70 (s, 2 H), 7.38-7.33 (m, 1 H), 7.14-7.03 (m, 4 H), 3.23-3.17 (m, 2 H), 3.11 (t, J=7.8 Hz, 2 H), 2.94-2.89 (m, 2 H), 2.71 (t, J=7.6 Hz, 2 H), 1.97 (quintet, J=7.6 Hz, 2 H); $^{13}$C NMR (126 MHz; DMSO-d$_6$): δ (163.2+161.3, 1 C), 154.0 (1 C), (143.72+143.66, 1 C), 142.8 (1 C), 134.6 (1 C), 134.1 (1 C), 133.3 (1 C), (130.31+130.25, 1 C), 128.2 (1 C), (124.47+124.45, 1 C), 120.9 (1 C), 117.5 (1 C), (115.09+114.93, 1 C), 114.0, (112.95+112.78, 1 C), 47.3 (1 C), 46.1 (1 C), 31.5 (1 C), 30.9 (1 C), 26.8 (1 C); ESIMS m/z (rel. intensity) 325 (MH$^+$, 100); HRMS calcd for $C_{20}H_{22}FN_3$: 323.1798. found: 323.1803.

Example 31

Purified NOS Enzyme Assays. Rat and human nNOS, murine macrophage iNOS, and bovine eNOS were recombinant enzymes, expressed in *E. coli* and purified as previously reported in the literature. To test for enzyme inhibition, the hemoglobin capture assay was used to measure nitric oxide production. The assay was performed at 37° C. in HEPES buffer (100 mM, with 10% glycerol, pH 7.4) in the presence of 10 μM L-arginine. Also included were 100 μM NADPH, 0.83 mM CaCl$_2$, approximately 320 units/mL of calmodulin, 10 μM tetrahydrobiopterin, and human oxyhemoglobin (3 μM). For iNOS, CaCl$_2$ and calmodulin were omitted and replaced with HEPES buffer (as neither are required for activation of iNOS). This assay was performed in 96-well plates using a Synergy 4 BioTek hybrid reader, and the dispensing of NOS enzyme and hemoglobin were automated; after 30 sec (maximum delay), NO production was read by monitoring the absorbance at 401 nm (resulting from the conversion of oxyhemoglobin to methemoglobin). Kinetic readouts were performed for 3 or 5 min. Each compound was assayed at least in duplicate, and nine concentrations (500 μM-50 nM or 100 μM-10 nM for eNOS and iNOS; 50 μM to 5 nM for nNOS) were used to construct dose-response curves. IC$_{50}$ values were calculated by non-linear regression using GraphPad Prism software, and K$_i$ values were obtained using the Cheng-Prusoff equation [K$_i$=IC$_{50}$/(1+[S]/K$_m$)] using the following K$_m$ values: 1.3 (rat nNOS), 1.6 (human nNOS), 8.2 (murine macrophage iNOS) and 1.7 μM (bovine eNOS).

Example 32

Inhibitor Complex Crystal Preparation. The nNOS or eNOS heme domain proteins used for crystallographic studies were produced by limited trypsin digest from the corresponding full length enzymes and further purified through a Superdex 200 gel filtration column (GE Healthcare) as described previously. The nNOS heme domain (at 9 mg/mL containing 20 mM histidine), or the eNOS heme domain (at 12 mg/mL containing 2 mM imidazole) were used for the sitting drop vapor diffusion crystallization setup under conditions previously reported. Fresh crystals (1-2 days old) were first passed stepwise through cryoprotectant solutions and then soaked with 10 mM inhibitor for 4-6 h at 4° C. before being flash cooled with liquid nitrogen.

Example 33

X-ray Diffraction Data Collection, Data Processing, and Structural Refinement. The cryogenic (100 K) X-ray diffraction data were collected remotely at the Stanford Synchrotron Radiation Lightsource (SSRL) or Advanced Light Source (ALS) through the data collection control software Blu-Ice and a crystal mounting robot. When a Q315r CCD detector was used, 90-100° of data were typically collected with 0.5° per frame. If a Pilatus pixel array detector was used, 120-130° of fine-sliced data were collected with 0.2° per frame. Raw CCD data frames were indexed, integrated, and scaled using HKL2000, but the pixel array data were processed with XDS and scaled with Scala. The binding of inhibitors was detected by the initial difference Fourier maps calculated with REFMAC. The inhibitor molecules were then modeled in COOT and refined using REFMAC. Disordering in portions of inhibitors bound in the NOS active sites was often observed, sometimes resulting in poor density quality. However, partial structural features usually could still be visible if the contour level of the sigmaA weighted 2 m|Fo|–D|Fc| map dropped to 0.5 σ, which afforded the building of reasonable models into the disordered regions. Water molecules were added in REFMAC and checked by COOT. The TLS protocol was implemented in the final stage of refinements with each subunit as one TLS group. The omit Fo–Fc density maps were calculated by repeating the last round of TLS refinement with inhibitor coordinate removed from the input PDB file to generate the map coefficients DELFWT and SIGDELFWT. The refined structures were validated in COOT before deposition in the RCSB protein data bank.

Example 34

Caco-2 Permeability Assay. Caco-2 monolayer assays were performed by Apredica, Inc (Watertown, Mass.) using the following standard procedure: Caco-2 cells, grown in tissue culture flasks, were trypsinized, re-suspended, and grown and differentiated in 96-well plates for three weeks; monolayer formation was determined by measuring transport of Lucifer yellow, an impermeable dye. All assays were performed at a concentration of 10 μM for 2 h. For apical to basolateral (A->B) permeability, compounds were added on the apical side (A), with permeation determined at the receiving (basolateral, B) side, where the receiving buffer was removed for analysis by LC/MS/MS using an Agilent 6410 mass spectrometer (ESI, MRM mode) coupled with an Agilent 1200 HPLC. Buffers used were 100 μM Lucifer yellow in transport buffer (1.98 g/L glucose in 10 mM HEPES, 1× Hank's Balanced Salt Solution, pH 6.5) (apical side) and tranport buffer, pH 7.4 (basolateral side). Apparent permeability ($P_{app}$) is expressed using the following equation: $P_{app}$= (dQ/dt)/$C_0$A, where the numerator is the rate of permeation, $C_o$ is initial concentration, and A is the monolayer area. For bidirectional permeability, the efflux ratio was defined as $P_{app}$ (B->A)/$P_{app}$ (A->B); high efflux ratio values (>3) indicate that a compound may be a substrate for P-gp or other active transport systems.

While the principles of this invention have been described in connection with specific embodiments, it should be understood that these descriptions are added only by way of example and are not intended to limit, in any way, the scope of this application. For instance, the present invention can include compounds with one or more substituents (e.g., alkyl, haloalkyl, etc.) on the quinoline ring (e.g., at the 4-position, etc.) and/or on the phenyl tail moiety, such compounds as would be understood by those skilled in the art made aware of this invention and prepared using synthetic techniques of the sort described herein or straight-forward modifications thereof. Regardless, compounds of this invention can be utilized as described herein and as probes for further study of nNOS or pathways dependent upon nNOS or modulated or otherwise affected by nNOS inhibition.

We claim:
1. A compound of a formula

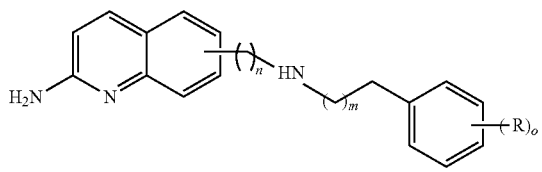

wherein n is an integer selected from 1-2; m is an integer selected from 1-3; R is selected from chloro and fluoro groups; and o is an integer selected from 0-2, or a salt thereof.

2. The compound of claim 1 wherein the sum of n and m is 4-5.

3. The compound of claim 1 wherein R is F, and o is 1.

4. The compound of claim 3 wherein F is meta to said alkyleneamine moiety.

5. The compound of claim 1 wherein said quinoline moiety is substituted at the 7-position thereof, with said arylalkyleneaminealkylene moiety.

6. The compound of claim 1 wherein said compound is an ammonium salt.

7. The compound of claim 6 wherein said salt has a counter ion that is the conjugate base of a protic acid.

8. A compound of a formula

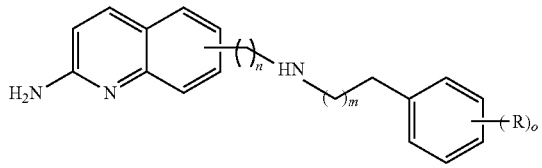

wherein n is an integer selected from 1-2; m is an integer selected from 1-3; R is selected from chloro and fluoro groups; and o is an integer selected from 0-2, or a salt thereof.

9. The compound of claim 8 wherein the sum of n and m is 4-5.

10. The compound of claim 9 wherein R is F, and o is 1.

11. The compound of claim 10 wherein F is meta to said alkyleneamine moiety.

12. The compound of claim 8 wherein said compound is an ammonium salt.

13. The compound of claim 12 wherein said salt has a counter ion that is the conjugate base of protic acid.

14. A compound of a formula

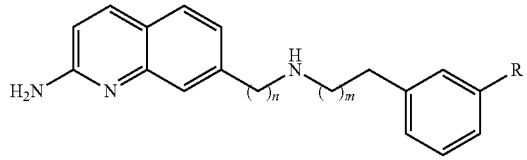

wherein n is an integer selected from 1-2; m is an integer from 2-3, providing where m is 3, n is 1; and R is selected from Cl and F, or a salt thereof.

15. The compound of claim 14 wherein the sum of n and m is 4.

16. The compound of claim 15 wherein R is F.

17. The compound of claim 14 wherein said compound is an ammonium salt.

18. The compound of claim 17 wherein said salt has a counter ion that is the conjugate base of a protic acid.

19. A method of modulating nitric oxide synthase activity, said method comprising contacting a nitric oxide synthase with an effective amount of a compound of claim 8.

20. The method of claim 19 wherein the sum of n and m is 4-5.

21. The method of claim 20 wherein R is meta to the alkyleneamine moiety of said compound.

22. A method of inhibiting a nitric oxide synthase, said method comprising:
providing a compound of claim 14; and
contacting said compound with a nitric oxide synthase, said compound in an amount effective to inhibit nitric oxide synthase activity, thereby reducing nitric oxide production.

23. The method of claim 22 wherein the sum of n and m is 4.

24. The method of claim 23 selective for inhibition of neuronal nitric oxide synthase.

25. The method of claim 22 wherein said compound is provided in a pharmaceutical composition.

26. A compound of a formula

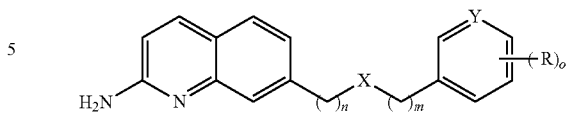

wherein X is selected from O and NH; Y is selected from CH and N; n is an integer selected from 1-2; m is an integer selected from 0-3; o is an integer selected from 0-3; and each R is independently selected from halo, alkyl, haloalkyl, alkoxy, cyano, amino, N-alkylamino, N,N-dialkylamino, aminealkyl, N-substituted and oxa-substituted aminealkyl moieties, or a salt thereof.

27. The compound of claim 26 wherein X is NH and Y is CH.

28. The compound of claim 27 wherein n is 1 and m is 0-1.

29. The compound of claim 26 wherein R is selected from fluoro, chloro, cyano, methoxy, N-alkylamine, N,N-dialkylamine, alkyl, aminealkyl, N-alkylaminealkyl and N,N-dialkylaminealkyl moieties.

30. The compound of claim 26 wherein X is O.

31. The compound of claim 30 wherein n is 1 and m is 0.

32. The compound of claim 31 wherein R is selected from fluoro, chloro, cyano, methoxy, N-methylamine, N,N-dimethylamine, alkyl, aminealkyl, N-methylaminealkyl and N,N-dimethylaminealkyl moieties.

33. The compound of claim 30 wherein Y is N and R is selected from N-methylaminealkyl and N,N-dimethylaminealkyl moieties.

34. A compound of a formula

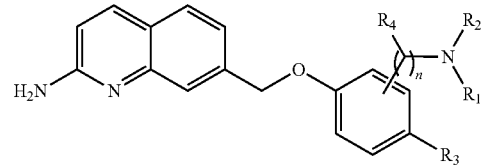

wherein $R_1$ and $R_2$ are independently selected from H and methyl moieties; $R_3$ is selected from halo, alkyl, haloalkyl, alkoxy, cyano, amine, N-methylamine, N,N-dimethylamine, alkyl, aminealkyl, N-methylaminealkyl and N,N-dimethylaminealkyl moieties; n is an integer selected from 0-3; and each $R_4$ is independently selected from H and methyl moieties, or a salt thereof.

35. The compound of claim 34 wherein $R_3$ is selected from halo and cyano moieties.

* * * * *